United States Patent
Talmadge

[19]

[11] Patent Number: 5,877,276
[45] Date of Patent: *Mar. 2, 1999

[54] POLYPEPTIDE AGONISTS FOR HUMAN INTERLEUKIN-8

[75] Inventor: James E. Talmadge, Bellevue, Nebr.

[73] Assignee: The Board of Regents of the University of Nebraska, Lincoln, Nebr.

[ * ] Notice: The term of this patent shall not extend beyond the expiration date of Pat. No. 5,627,156.

[21] Appl. No.: 847,696

[22] Filed: Apr. 28, 1997

Related U.S. Application Data

[63] Continuation-in-part of Ser. No. 311,307, Sep. 23, 1994, Pat. No. 5,627,156.

[51] Int. Cl.$^6$ .......................... A61K 38/10; A61K 38/16; C07K 7/08; C07K 14/00
[52] U.S. Cl. .............................. 530/324; 514/12; 514/13; 514/14; 530/325; 530/326; 530/327; 930/141
[58] Field of Search ..................... 530/324, 325, 530/326, 327; 514/12, 13, 14; 930/140, 141; 424/85.1, 85.2

[56] References Cited

U.S. PATENT DOCUMENTS

| | | | |
|---|---|---|---|
| 5,079,228 | 1/1992 | Cohen et al. | 514/12 |
| 5,627,156 | 5/1997 | Talmadge | 514/13 |

FOREIGN PATENT DOCUMENTS

| | | |
|---|---|---|
| 92/04372 | 3/1992 | WIPO . |
| 94/12537 | 6/1994 | WIPO . |
| 95/35376 | 12/1995 | WIPO . |

OTHER PUBLICATIONS

Hayashi et al. Synthetic Hexa– and Heptapetides . . . J. Immunol. Vol. 154, pp. 814–824, 1995.

*Primary Examiner*—Jeffrey E. Russel
*Attorney, Agent, or Firm*—Dann, Dorfman, Herrell and Skillman

[57] ABSTRACT

Polypeptides derived from human interleukin-8 (IL-8) which act as therapeutic agents for the therapy of neoplastic (both solid and leukemic) and infectious diseases such as bacterial, fungal, viral and parasitic.

1 Claim, 10 Drawing Sheets

Dose of Analog 1 (μg/animal)

SEQUENCE LISTING ( 1 ) GENERAL INFORMATION:

( i i i ) NUMBER OF SEQUENCES: 12

( 2 ) INFORMATION FOR SEQ ID NO:1:

( i ) SEQUENCE CHARACTERISTICS:
        ( A ) LENGTH: 17 amino acids
        ( B ) TYPE: amino acid
        ( C ) STRANDEDNESS: Not Relevant
        ( D ) TOPOLOGY: Not Relevant ( i i ) MOLECULE TYPE: peptide ( i i i ) HYPOTHETICAL: NO ( i v ) ANTI-SENSE: NO (ix) FEATURE:
        (A) NAME/KEY: Modified-site
        (B) LOCATION: 4..6
        (D) OTHER INFORMATION: /note= "The Xaa in positions 4 and 6
            in the peptide may be aminobutyric acid, homocysteine,
            cysteine or diaminosuberic acid."

(xi) SEQUENCE DESCRIPTION: SEQ ID NO:1:

Glu  Leu  Arg  Xaa  Gln  Xaa  Ile  Lys  Thr  Tyr  Ser  Lys  Pro  Phe  His  Pro
    1                   5                        10                       15

Lys (2) INFORMATION FOR SEQ ID NO:2:

(i) SEQUENCE CHARACTERISTICS:
        (A) LENGTH: 14 amino acids
        (B) TYPE: amino acid
        (C) STRANDEDNESS: Not Relevant
        (D) TOPOLOGY: Not Relevant (ii) MOLECULE TYPE: peptide (iii) HYPOTHETICAL: NO (iv) ANTI-SENSE: NO (ix) FEATURE:
        (A) NAME/KEY: Modified-site
        (B) LOCATION: 4..6
        (D) OTHER INFORMATION: /note= "The Xaa in positions 4 and 6
            in the peptide may be aminobutyric acid, homocysteine,
            cysteine or diaminosuberic acid."

(xi) SEQUENCE DESCRIPTION: SEQ ID NO:2:

Glu  Leu  Arg  Xaa  Gln  Xaa  Ile  Lys  Thr  Tyr  Ser  Lys  Pro  Phe
    1                   5                        10

(2) INFORMATION FOR SEQ ID NO:3:

(i) SEQUENCE CHARACTERISTICS:
        (A) LENGTH: 16 amino acids
        (B) TYPE: amino acid
        (C) STRANDEDNESS: Not Relevant
        (D) TOPOLOGY: Not Relevant (ii) MOLECULE TYPE: peptide (iii) HYPOTHETICAL: NO (iv) ANTI-SENSE: NO (ix) FEATURE:
        (A) NAME/KEY: Modified-site
        (B) LOCATION: 4..6
        (D) OTHER INFORMATION: /note= "The Xaa in positions 4 and 6
            in the peptide may be aminobutyric acid, homocysteine,
            cysteine or diaminosuberic acid."

(xi) SEQUENCE DESCRIPTION: SEQ ID NO:3:

Glu  Leu  Arg  Xaa  Gln  Xaa  Leu  Gln  Thr  Leu  Gln  Gly  Ile  His  Pro  Lys
    1                   5                        10                       15

(2) INFORMATION FOR SEQ ID NO:4:

(i) SEQUENCE CHARACTERISTICS:
        (A) LENGTH: 16 amino acids
        (B) TYPE: amino acid
        (C) STRANDEDNESS: Not Relevant
        (D) TOPOLOGY: Not Relevant (ii) MOLECULE TYPE: peptide ( i i i ) HYPOTHETICAL: NO ( i v ) ANTI-SENSE: NO ( i x ) FEATURE:
    ( A ) NAME/KEY: Modified-site
    ( B ) LOCATION: 4..6
    ( D ) OTHER INFORMATION: /note= "The Xaa in positions 4 and 6
        in the peptide may be aminobutyric acid, homocysteine,
        cysteine or diaminosuberic acid."

( x i ) SEQUENCE DESCRIPTION: SEQ ID NO:4:

| Glu | Leu | Arg | Xaa | Gln | Xaa | Leu | Gln | Thr | Leu | Gln | Gly | Ile | His | Leu | Lys |
|---|---|---|---|---|---|---|---|---|---|---|---|---|---|---|---|
| 1 | | | | 5 | | | | | 10 | | | | | 15 | |

( 2 ) INFORMATION FOR SEQ ID NO:5:

( i ) SEQUENCE CHARACTERISTICS:
        ( A ) LENGTH: 16 amino acids
        ( B ) TYPE: amino acid
        ( C ) STRANDEDNESS: Not Relevant
        ( D ) TOPOLOGY: Not Relevant ( i i ) MOLECULE TYPE: peptide ( i i i ) HYPOTHETICAL: NO ( i v ) ANTI-SENSE: NO ( i x ) FEATURE:
        ( A ) NAME/KEY: Modified-site
        ( B ) LOCATION: 4..6
        ( D ) OTHER INFORMATION: /note= "The Xaa in positions 4 and 6
            in the peptide may be aminobutyric acid, homocysteine,
            cysteine or diaminosuberic acid."

( x i ) SEQUENCE DESCRIPTION: SEQ ID NO:5:

| Glu | Leu | Arg | Xaa | Gln | Xaa | Leu | Gln | Thr | Met | Thr | Gly | Val | His | Leu | Lys |
|---|---|---|---|---|---|---|---|---|---|---|---|---|---|---|---|
| 1 | | | | 5 | | | | | 10 | | | | | 15 | |

( 2 ) INFORMATION FOR SEQ ID NO:6:

( i ) SEQUENCE CHARACTERISTICS:
        ( A ) LENGTH: 15 amino acids
        ( B ) TYPE: amino acid
        ( C ) STRANDEDNESS: Not Relevant
        ( D ) TOPOLOGY: Not Relevant ( i i ) MOLECULE TYPE: peptide ( i i i ) HYPOTHETICAL: NO ( i v ) ANTI-SENSE: NO ( i x ) FEATURE:
        ( A ) NAME/KEY: Modified-site
        ( B ) LOCATION: 4..6
        ( D ) OTHER INFORMATION: /note= "The Xaa in positions 4 and 6
            in the peptide may be aminobutyric acid, homocysteine,
            cysteine or diaminosuberic acid."

( x i ) SEQUENCE DESCRIPTION: SEQ ID NO:6:

| Glu | Leu | Arg | Xaa | Gln | Xaa | Leu | Gln | Thr | Leu | Gln | Gly | His | Leu | Lys |
|---|---|---|---|---|---|---|---|---|---|---|---|---|---|---|
| 1 | | | | 5 | | | | | 10 | | | | | 15 |

( 2 ) INFORMATION FOR SEQ ID NO:7:

( i ) SEQUENCE CHARACTERISTICS:
        ( A ) LENGTH: 16 amino acids
        ( B ) TYPE: amino acid
        ( C ) STRANDEDNESS: Not Relevant
        ( D ) TOPOLOGY: Not Relevant ( i i ) MOLECULE TYPE: peptide (  i i i  )  HYPOTHETICAL: NO (  i v  )  ANTI-SENSE: NO (  i x  )  FEATURE:
    ( A ) NAME/KEY: Modified-site
    ( B ) LOCATION: 4..6
    ( D ) OTHER INFORMATION: /note= "The Xaa in positions 4 and 6
        in the peptide may be aminobutyric acid, homocysteine,
        cysteine or diaminosuberic acid."

(  x i  )  SEQUENCE DESCRIPTION: SEQ ID NO:7:

```
Glu  Leu  Arg  Xaa  Met  Xaa  Ile  Lys  Thr  Thr  Ser  Gly  Ile  His  Pro  Lys
 1                   5                        10                       15
```

( 2 ) INFORMATION FOR SEQ ID NO:8:

( i ) SEQUENCE CHARACTERISTICS:
    ( A ) LENGTH: 17 amino acids
    ( B ) TYPE: amino acid
    ( C ) STRANDEDNESS: Not Relevant
    ( D ) TOPOLOGY: Not Relevant (  i i  ) MOLECULE TYPE: peptide (  i i i  ) HYPOTHETICAL: NO (  i v  ) ANTI-SENSE: NO (  i x  ) FEATURE:
    ( A ) NAME/KEY: Modified-site
    ( B ) LOCATION: 4..6
    ( D ) OTHER INFORMATION: /note= "The Xaa in positions 4 and 6
        in the peptide may be aminobutyric acid, homocysteine,
        cysteine or diaminosuberic acid."

(  x i  ) SEQUENCE DESCRIPTION: SEQ ID NO:8:

```
Glu  Leu  Arg  Xaa  Gln  Xaa  Ile  Ser  Thr  His  Ser  Lys  Phe  Ile  His  Pro
 1                   5                        10                       15
Lys
```

( 2 ) INFORMATION FOR SEQ ID NO:9:

( i ) SEQUENCE CHARACTERISTICS:
    ( A ) LENGTH: 17 amino acids
    ( B ) TYPE: amino acid
    ( C ) STRANDEDNESS: Not Relevant
    ( D ) TOPOLOGY: Not Relevant (  i i  ) MOLECULE TYPE: peptide (  i i i  ) HYPOTHETICAL: NO (  i v  ) ANTI-SENSE: NO (  i x  ) FEATURE:
    ( A ) NAME/KEY: Modified-site
    ( B ) LOCATION: 4..6
    ( D ) OTHER INFORMATION: /note= "The Xaa in positions 4 and 6
        in the peptide may be aminobutyric acid, homocysteine,
        cysteine or diaminosuberic acid."

(  x i  ) SEQUENCE DESCRIPTION: SEQ ID NO:9:

```
Glu  Leu  Arg  Xaa  Gln  Xaa  Ile  Lys  Thr  Tyr  Ser  Lys  Pro  Phe  His  Pro
 1                   5                        10                       15
His
```

( 2 ) INFORMATION FOR SEQ ID NO:10:

( i ) SEQUENCE CHARACTERISTICS:
    ( A ) LENGTH: 16 amino acids (B) TYPE: amino acid
(C) STRANDEDNESS: Not Relevant
(D) TOPOLOGY: Not Relevant (ii) MOLECULE TYPE: peptide (iii) HYPOTHETICAL: NO (iv) ANTI-SENSE: NO (ix) FEATURE:
(A) NAME/KEY: Modified-site
(B) LOCATION: 4..6
(D) OTHER INFORMATION: /note= "The Xaa in positions 4 and 6 in the peptide may be aminobutyric acid, homocysteine, cysteine or diaminosuberic acid."

(xi) SEQUENCE DESCRIPTION: SEQ ID NO:10:

| Glu | Leu | Arg | Xaa | Gln | Xaa | Leu | Gln | Thr | Val | Ala | Gly | Ile | His | Phe | Lys |
|---|---|---|---|---|---|---|---|---|---|---|---|---|---|---|---|
| 1 | | | | 5 | | | | | 10 | | | | | 15 | |

(2) INFORMATION FOR SEQ ID NO:11:

(i) SEQUENCE CHARACTERISTICS:
(A) LENGTH: 16 amino acids
(B) TYPE: amino acid
(C) STRANDEDNESS: Not Relevant
(D) TOPOLOGY: Not Relevant (ii) MOLECULE TYPE: peptide (iii) HYPOTHETICAL: NO (iv) ANTI-SENSE: NO (ix) FEATURE:
(A) NAME/KEY: Modified-site
(B) LOCATION: 4..6
(D) OTHER INFORMATION: /note= "The Xaa in positions 4 and 6 in the peptide may be aminobutyric acid, homocysteine, cysteine or diaminosuberic acid."

(xi) SEQUENCE DESCRIPTION: SEQ ID NO:11:

| Glu | Leu | Arg | Xaa | Val | Xaa | Leu | Gln | Thr | Thr | Gln | Gly | Val | His | Pro | Lys |
|---|---|---|---|---|---|---|---|---|---|---|---|---|---|---|---|
| 1 | | | | 5 | | | | | 10 | | | | | 15 | |

(2) INFORMATION FOR SEQ ID NO:12:

(i) SEQUENCE CHARACTERISTICS:
(A) LENGTH: 17 amino acids
(B) TYPE: amino acid
(C) STRANDEDNESS: Not Relevant
(D) TOPOLOGY: Not Relevant (ii) MOLECULE TYPE: peptide (iii) HYPOTHETICAL: NO (iv) ANTI-SENSE: NO (ix) FEATURE:
(A) NAME/KEY: Modified-site
(B) LOCATION: 4..6
(D) OTHER INFORMATION: /note= "The Xaa in positions 4 and 6 in the peptide may be aminobutyric acid, homocysteine, cysteine or diaminosuberic acid."

(ix) FEATURE:
(A) NAME/KEY: Modified-site
(B) LOCATION: 5
(D) OTHER INFORMATION: /label=Xaa1
/ note= "Xaa1 in the fifth position may be Gln, Leu, Thr, Met, or Val."

(ix) FEATURE:
(A) NAME/KEY: Modified-site (B) LOCATION: 7
(D) OTHER INFORMATION: /label=Xaa2
/note= "Xaa2 in the seventh position may be Ile, Val, or Leu."

(ix) FEATURE:
(A) NAME/KEY: Modified-site
(B) LOCATION: 8
(D) OTHER INFORMATION: /label=Xaa3
/note= "Xaa3 in the eighth position may be Lys, Gln, or Ser."

(ix) FEATURE:
(A) NAME/KEY: Modified-site
(B) LOCATION: 9
(D) OTHER INFORMATION: /label=Xaa4
/note= "Xaa4 at the ninth position may be Thr or Ile."

(ix) FEATURE:
(A) NAME/KEY: Modified-site
(B) LOCATION: 10
(D) OTHER INFORMATION: /label=Xaa5
/note= "Xaa5 at position 10 may be Tyr, Thr, Asn, Leu, Met, Val or His."

(ix) FEATURE:
(A) NAME/KEY: Modified-site
(B) LOCATION: 11
(D) OTHER INFORMATION: /label=Xaa6
/note= "Xaa6 in the eleventh position may be Ser, Leu, Met, Gln, Val, Thr or Ala."

(ix) FEATURE:
(A) NAME/KEY: Modified-site
(B) LOCATION: 12
(D) OTHER INFORMATION: /label=Xaa7
/note= "Xaa7 at position 12 may be Lys, Arg, His or Gly."

(ix) FEATURE:
(A) NAME/KEY: Modified-site
(B) LOCATION: 13
(D) OTHER INFORMATION: /label=Xaa8
/note= "Xaa8 position 13 may be absent or may be Phe, Gly, Ile, Val, His or Pro."

(ix) FEATURE:
(A) NAME/KEY: Modified-site
(B) LOCATION: 14
(D) OTHER INFORMATION: /label=Xaa9
/note= "Xaa9 at position 14 may be absent or may be Ile, Val, Phe or Gly."

(ix) FEATURE:
(A) NAME/KEY: Modified-site
(B) LOCATION: 15
(D) OTHER INFORMATION: /label=Xaa10
/note= "Xaa10 at position 15 may be absent or may be His, Arg, Asn or Lys."

(ix) FEATURE:
(A) NAME/KEY: Modified-site
(B) LOCATION: 16
(D) OTHER INFORMATION: /label=Xaa11
/note= "Xaa11 at position 16 may be absent or may be Pro, Leu or Phe."

(ix) FEATURE:
(A) NAME/KEY: Modified-site
(B) LOCATION: 17
(D) OTHER INFORMATION: /label=Xaa12
/note= "Xaa12 at position 17 may be absent or may be Lys, Arg or His."

(xi) SEQUENCE DESCRIPTION: SEQ ID NO:12:

Glu Leu Arg Xaa Xaa Xaa Xaa Xaa Xaa Xaa Xaa Xaa Xaa Xaa Xaa Xaa
1               5                       10                      15
Xaa

POLYPEPTIDE AGONISTS FOR HUMAN INTERLEUKIN-8

CROSS REFERENCE TO RELATED APPLICATION

This application is a continuation in part of application, Ser. No. 08/311,307, filed Sep. 23, 1994 which issued May 6, 1997 as U.S. Pat. No. 5,627,156, and which is incorporated herein by reference.

BACKGROUND OF THE INVENTION

The present invention relates to polypeptide agonists of the human cytokine interleukin 8 to other human alpha chemokines and to the method of using these agonists.

Interleukin 8 (IL-8) is a human cytokine that promotes the recruitment and activation of neutrophil leukocytes and represents one of several endogenous mediators of the acute inflammatory response. In the past it was variously termed neutrophil-activating factor, monocyte-derived neutrophil chemotactic factor, interleukin-8 (IL-8), and neutrophil-activating peptide-1. IL-8 has gained the widest acceptance and will be used herein.

The most abundant naturally occurring form of the IL-8 monomer is a 72-residue protein apparently derived by processing of a 99-residue precursor. Other proteins with related sequences, including neutrophil-activating peptide-2 and GROα (with melanoma growth stimulatory activity) are IL-8 homologues which have neutrophil-activating properties.

IL-8 is a member of the chemokine superfamily that is divided into two distinct function classes: alpha (α) and beta (β). The members of each class share an organizing primary sequence motif. The α members are distinguished by a C-X-C motif with the first two cysteines in the motif separated by an intervening residue. C-X-C chemokines are potent chemoattractants and activators for neutrophils, and are represented by IL-8. The β family chemokines have a C—C motif and are equally potent chemoattractants and activators of monocytes. It appears that the two sides of the chemokine family have clearly defined functions: the C-X-C subfamilies cannot activate monocytes while the C—C subfamily has no effect on neutrophils. Nonetheless these two families of chemokines have similar structures although fairly low sequence homology (30 to 35%). Proteins within the same family such as platelet factor four (PF-4) are structurally related to IL-8 (35% sequence identity) but lack the N terminal ELR sequence (Glu-Leu-Arg) which has been shown by site directed mutagenesis to be critical for IL-8 activity and thus, PF-4 has an entirely different profile of activity. Indeed, when the ELR sequence is added to the N-terminus of PF-4 it has been found that the modified protein has potent neutrophil activation and chemoattractant properties (Clark-Lewis, I; Dewald, B.; Geiser, T.; Moser, B.; Baggiolini, M.: Platelet factor 4 binds to interleukin 8 receptors and activates neutrophils when its N terminus is modified with Glu-Leu-Arg. Biochemistry 90:3574–3577, 1993). However this is not true for all of the chemokines since two of the proteins related to IL-8, γ interferon inducible protein (IP-10) and monocyte chemoattractant protein 1 (MCP-1) do not acquire neutrophil activating properties when the ELR structural determinants are added.

In studies by Clark-Lewis (Clark-Lewis, I., et al.: Structural requirements for interleukin-8 function identified by design of analogs and CXC chemokine hybrids. J Biol Chem 269:16075–16081, 1994) it was shown that conservative substitutions are accepted into the 10–22 region of IL-8 in contrast with the ELR motif (residues 4–6). They concluded that the disulfide bridges and the 30–35 turn provide a structural scaffold for the NH-2 terminal region which includes a primary receptor binding site (ELR motif) and secondary binding and conformational determinants similar to those seen in residues 10 through 22. Other studies using mutants of IL-8 and melanoma growth stimulating activity (MGSA) and recombinant IL-8 α/β receptors stably expressed in human cells demonstrated that there was a second site on the molecule responsible for binding. It appears that the carboxy terminus distal to amino acid 50 is not important in high affinity binding to the α receptor although both the amino and carboxy termini appear to be important for binding to the β receptor (Schraufstatter, I.S., et al., Multiple sites on IL-8 responsible for binding to α and β IL-8 receptors. J Immunol 151:6418–6428, 1993). In summary, it appears that there are at least two and maybe three regions responsible for binding on IL-8. Further, the specific contact pharmacophore may vary depending upon whether or not the α or the β receptor is being examined.

The in vitro effects of IL-8 on neutrophils are similar to those of other chemotactic agonists such as C5a and fMet-Leu-Phe and include induction of a transient rise in cytosolic free calcium, the release of granules containing degradative enzymes such as elastase, the respiratory $H_2O_2$ burst, neutrophil shape change, and chemotaxis. IL-8 appears to bind to at least one class of receptor sites on neutrophils with a frequency of approximately 64,000/cell and a $K_d$ of 0.2 nM.

The three-dimensional structure of IL-8 is known by two-dimensional NMR and x-ray diffraction techniques. The IL-8 monomer has antiparallel β strands followed by a single overlying COOH-terminal α helix. Two disulfide bridges, between cysteines 7 and 34, and between cysteines 9 and 50 seem to stabilize the tertiary structure. Residues 1–6 and the loop residues 7–18 seem to have little defined secondary structure. In solution, IL-8 is a noncovalent homodimer which is stabilized primarily by interactions between the β strands of the two monomers.

Examination of the three-dimensional structure indicates that following the cysteine at position 50, the residues form a type 1 β turn (at residues 51 to 55) followed by an amphipathic α helix (at residues 55 to 72) that transverses the β sheet. The hydrophobic face of the α helix interacts with and stabilizes the hydrophobic face of the β sheet. Some of the interactions are between the two subunits of the dimeric molecule.

Interleukin-8 has shown both anti-tumor and anti-infective therapeutic activity. IL-8 has been shown to induce the regression of macroscopic tumors in a model of peritoneal carcinomatosis in the rat. In this model IL-8 was shown to recruit PMN to the challenge site but did not enhance PMN infiltration of the tumor or the cytotoxic activity of PMN. Regardless, it did have significant therapeutic activity which may be secondary to PMN cytotoxicity and associated with other intermediate cells. It is suggested that lymphocytes could be involved since IL-8 has also demonstrated the ability to stimulate T-cell chemotaxisis. (Lejeune, P., et al.: Interleukin-8 has antitumor effects in the rat which are not associated with polymorphonuclear leukocyte cytotoxicity. Cancer Immunol Immunotherapy 38:167–170, 1994). Similarly, Interleukin-8 has shown therapeutic activity in nonneutropenic mice who received IL-8 shortly before challenge and at the site of infectious challenge with either *P. aeruginosa, Klebsiella-phenumoniae*, or *Plasmodium-berghei*. (Vogels, M. T., et al., Effects of Interleukin-8 on nonspecific resistance to infection in neutropenic and normal mice. Antimicrob-Agents-Chemother 37:276–280, 1993).

In other antitumor studies, IP-10, an alpha chemokine whose secretion is induced by IFN-γ and LPS, was genetically engineered into tumor cells. The expression of IP-10 by several tumor cell lines had no effect on the growth of these tumor cells in vitro but elicited a powerful host mediated anti-tumor effect in vivo. Indeed, tumors genetically engineered to secrete IP-10 elicited a T-lymphocyte dependent anti-tumor response resulting in the rejection of tumors in vivo. Animals injected with these tumor cells do not develop tumors or develop tumors which spontaneously regress. Further, tumors induced with the parent tumor cells admixed with IP-10 secreting tumor cells protect the animals against subsequent growth. This suggests that in addition to being chemotactic for T-cells (Clark-Lewis, I., et al., Structural requirements for Interleukin-8 function identified by design of analogs and CXC chemokine hybrids. J Biol Chem 269:16075–16081, 1994) alpha chemokines may also act as T-cell adjuvants and therapeutics via T-cell chemotaxis and/or augmentation (Luster, A. D., a CXC chemokine, elicits a potent thymus-dependent antitumor response in vivo. J Exp Med 178:1057–1064, 1993).

IL-8 has been previously produced through chemical synthesis (for example see: Clark-Lewis, et al., "Chemical Synthesis, Purification, and Characterization of Two Inflammatory Proteins; Neutrophil-Activating Peptide-1 (Interleukin-8) and Neutrophil-Activating Peptide-2" (1991) Biochemistry 30: 3128–3135) and by recombinant DNA methods (for example see: Herbert, et al., "Scanning Mutagenesis of Interleukin-8 Identifies A Cluster of Residues Required for Receptor Binding" (1991) J. Biol. Chem. 286: 18989–18994). In addition, it is known that IL-8 exists in several forms that vary at the $NH_2$-terminus, which have been detected in preparations purified from natural sources. These variations correspond to the predominant 72-residue form (which is generally considered to be the prototype IL-8 molecule); a 77-residue form having 5 additional NH2-terminus amino acids on each monomer; and, two shortened forms having residues 3–72 and 4–72 of the 72 amino acid form, respectively.

SUMMARY OF THE INVENTION

The present invention involves low molecular weight peptides which have agonistic activity for IL-8 or other alpha chemokines and have an amino acid sequence with the following formula (Sequence I.D. No. 12):

Glu-Leu-Arg-Cys-$Xaa_1$-Cys-$Xaa_2$-$Xaa_3$-$Xaa_4$-$Xaa_5$-$Xaa6$-$Xaa_7$-$Xaa_8$-$Xaa_9$-$Xaa_{10}$-$Xaa_{11}$-$Xaa_{12}$ wherein $Xaa_1$ is Gln, Leu, Thr, Met, or Val;

$Xaa_2$ is Ile, Leu, or Val;

$Xaa_3$ is Lys, Gln, or Ser;

$Xaa_4$ is Thr, or Ile;

$Xaa_5$ is Tyr, Thr, Asn, Leu, Met, Val, or His;

$Xaa_6$ is Ser, Leu, Met, Gln, Val, Ala, or Thr;

$Xaa_7$ is Lys, Arg, His, or Gly;

$Xaa_8$ is absent or is Phe, Gly, Val, His, Ile, or Pro;

$Xaa_9$ is absent or is Ile, Val, Phe, or Gly;

$Xaa_{10}$ is absent or is His, Arg, Lys, or Asn;

$Xaa_{11}$ is absent or is Pro, Phe, Lys, or Leu; and $Xaa_{12}$ is absent or is Lys, Arg, or His.

More particularly, the preferred embodiment of the present invention comprises an amino acid sequence substantially equivalent to Glu-Leu-Arg-Cys-Gln-Cys-Ile-Lys-Thr-Tyr-Ser-Lys-Pro-Phe-His-Pro-Lys (Sequence I.D. No. 1) as well as similar analogs having additional N-terminal amino acids. These polypeptides act as anti-cancer and anti-infective agents for the therapy of leukemia and solid tumors and metastatic disease. These embodiments also have anti-infective therapeutic activity for viral, bacterial, fungal, yeast and parasitic infections.

In contrast to the claimed invention in PCT/CA92/00528 which describes a 77 amino acid antagonist to IL-8, the embodiment of the present invention is a low molecular weight peptide agonist which contains between 12 and 27 amino acids in length. This allows for more rapid and extensive tissue distribution of the drug on administration as compared to a 72 amino acid therapeutic. Further, this invention substantially increases the purity of the product through reduced errors inherent to the manufacture of a large protein. In addition this invention has a significant reduction in the cost of goods as compared to the natural IL-8. Based on the homogeneity of the alpha chemokines, both sequence and three dimensional, antagonists for both known and additional alpha chemokines can be derived based on the present invention.

In embodiments of the invention, the polypeptide is modified selectively to provide additional agonists of IL-8. In one particular embodiment, IL-8 agonists may include peptides truncated by 3 amino acid residues at the C terminus by deletion. In another particular embodiment, agonists for IL-8 or other alpha chemokines include cysteine substitutions by aminobutyric acid, homocysteine or diaminosuberic acid.

Several low molecular weight peptide analogs of IL-8 were investigated and it has been determined unexpectedly that truncation of the form of IL-8, particularly in the N terminal region thereof, yields IL-8 low molecular weight peptide analogs having therapeutically useful properties. More particularly, the IL-8 low molecular weight peptide analogs of the present invention comprise an amino acid sequence with biological activity that substantially competes for IL-8 binding and is based on the IL-8 sequence beginning at residue 4 and continuing through residue 17 or 20.

The inventor herein has investigated several low molecular weight peptide analogs of IL-8 and has discovered that truncation of the form of IL-8, particularly in the C-terminal region thereof, yields IL-8 peptidal mimetics having the therapeutically useful properties of anti-neoplastic and anti-infective drugs. More particularly, the IL-8 low molecular weight peptide analogs of the present invention comprises an amino acid sequence with biological activity substantially equivalent to the IL-8 sequence beginning at residue 4 and continuing through residue 20, wherein at least the N-terminal residues found to be critical for neutrophil binding and stimulation, i.e., Glu-4, Leu-5, Arg-6 are contained at the N-terminal region.

In addition, IL-8 analogs may include an additional two or three residues at the amino terminus of the 20 residue peptide so as to provide the 1–20 forms which are also useful as IL-8 agonists. In addition, significant biological activity is associated with low molecular weight peptide analogs from residue 4–15 resulting in a 12 amino acid peptide with agonist activity for IL-8.

Accordingly, this invention provides a biologically active human IL-8 analog or low molecular weight peptide analogs having an amino acid sequence substantially equivalent to the IL-8 4–20 or 4–15 sequence beginning at residue 4 and continuing to residue 15 or 20.

This invention also provides methods of use of the aforementioned analogs. In addition, this invention also provides methods of use of additional low molecular weight peptide analogs with conservative substitutions and/or additions in the sequence.

DETAILED DESCRIPTION OF THE INVENTION

Figure 1:
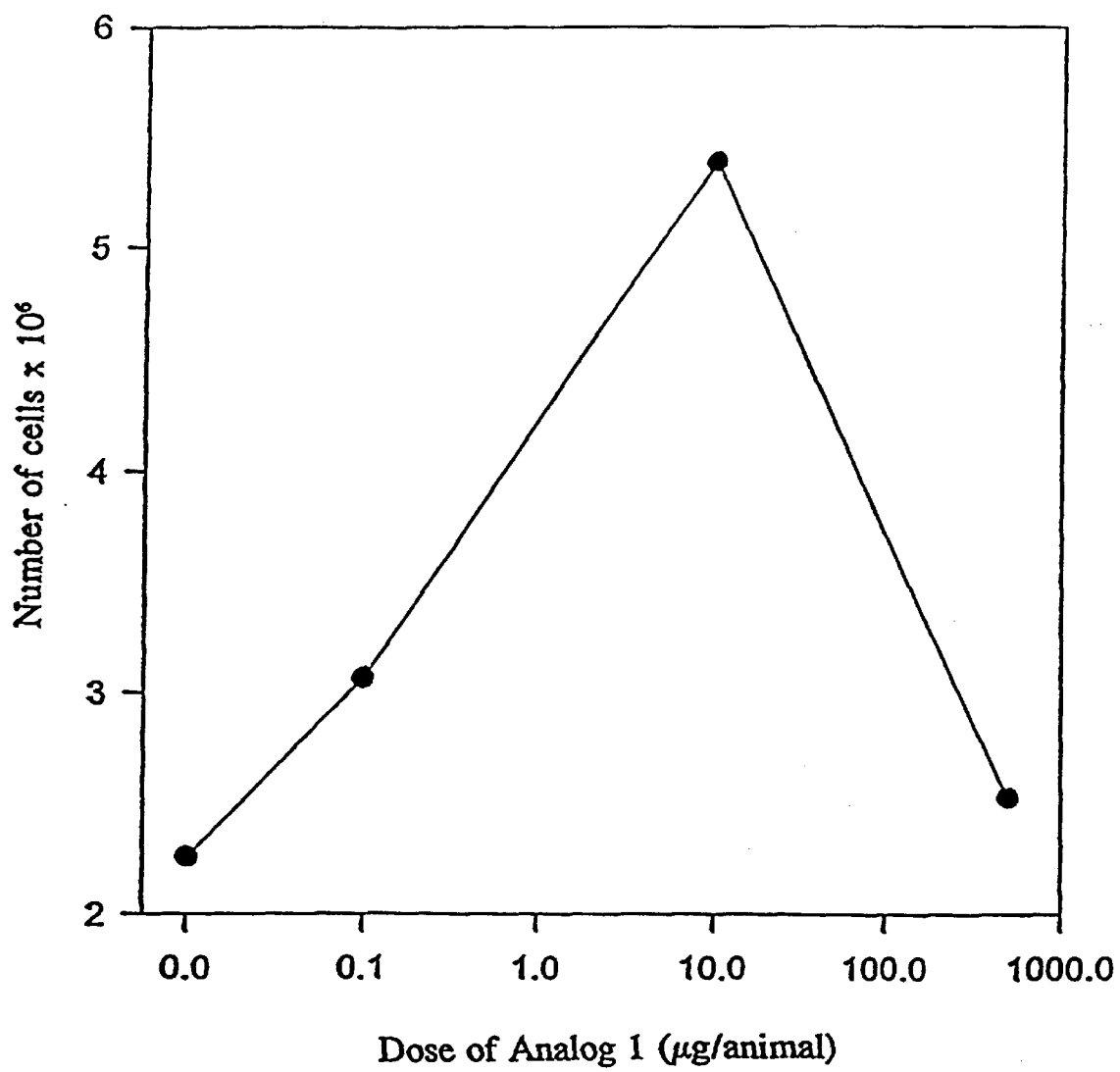
FIG. 1: A graph of a dose response curve showing the chemotactic effects of a single i.p. injection of Analog 1 in increasing concentrations. X axis represents the dose of Analog 1 in μg/animal; Y axis depicts cell number×$10^6$ in the peritoneum.

In order to provide an understanding of several of the terms used in the specification and claims, the following definitions are provided:

Biological activity—The term biological activity is a function or set of functions performed by a molecule in a biological context (i.e., in an organism or an in vitro surrogate or facsimile model). For IL-8 or other alpha chemokines, biological activity is characterized by its chemotactic activity (preferably PMNs but may also include T lymphocytes and/or monocytes/macrophages). It may also include second messenger and/or increases in elastase activity by PMNS.

A low molecular weight peptide analog—This identifies a natural or mutant (mutated) analog of a protein, comprising a linear or discontinuous series of fragments of that protein and which may have one or more amino acids replaced with other amino acids and which has altered, enhanced or diminished biological activity when compared with the parent or non-mutated protein.

Substantially equivalent biological activity—is that profile of activity which defines IL-8 or other alpha chemokine. In in vitro surrogate models this may include chemotaxsis of PMNs, T lymphocytes or monocytes; Ca signal transduction; or increases in elastase activity. In vivo this would be defined as the chemotaxsis of PMNs to a localized site for example the peritoneum following ip injection or to the peripheral blood.

TABLE 1

The amino acids are identified in the present application according to the three-letter or one-letter abbreviations in the following Table 1:

| | 3-letter Abbreviation | 1-letter Abbreviation |
|---|---|---|
| L-Alanine | Ala | A |
| L-Arginine | Arg | R |
| L-Asparagine | Asn | N |
| L-Aspartic Acid Amino Acid | Asp | D |
| L-Cysteine | Cys | C |
| L-Glutamine | Gln | Q |
| L-Glutamic Acid | Glu | E |
| Glycine | Gly | G |
| L-Histidine | His | H |
| L-Isoleucine | Ile | I |
| L-Leucine | Leu | L |
| L-Methionine | Met | M |
| L-Norleucine | NorLeu | J |
| L-Ornithine | Orn | O |
| L-Phenylalanine | Phe | F |
| L-Proline | Pro | P |
| L-Serine | Ser | S |
| L-Threonine | Thr | T |
| L-Tryptophan | Trp | W |
| L-Tyrosine | Tyr | Y |
| L-Valine | Val | V |
| "Asx" means Asp or Asn | | |
| "Glx" means Glu or Gln | | |
| L-Lysine | Lys | K |

The present invention includes peptide sequences having the following formula (Sequence I.D. No. 12):

Glu-Leu-Arg-Cys-$Xaa_1$-Cys-$Xaa_2$-$Xaa_3$-$Xaa_4$-$Xaa_5$-$Xaa_6$-$Xaa_7$-$Xaa_8$-$Xaa_9$-$Xaa_{10}$-$Xaa_{11}$-$Xaa_{12}$ wherein $Xaa_1$ is Gln, Leu, Thr, Met, or Val;

$Xaa_2$ is Ile, Leu, or Val;

$Xaa_3$ is Lys, Gln, or Ser;

$Xaa_4$ is Thr, or Ile;

$Xaa_5$ is Tyr, Thr, Asn, Leu, Met, Val, or His;

$Xaa_6$ is Ser, Leu, Met, Gln, Val, Ala, or Thr;

$Xaa_7$ is Lys, Arg, His, or Gly;

$Xaa_8$ is absent or is Phe, Gly, Val, His, Ile, or Pro;

$Xaa_9$ is absent or is Ile, Val, Phe, or Gly;

$Xaa_{10}$ is absent or is His, Arg, Lys, or Asn;

$Xaa_{11}$ is absent or is Pro, Phe, Lys, or Leu; and $Xaa_{12}$ is absent or is Lys, Arg, or His.

TABLE 2

Exemplary of the analogs of the present invention are the following:

Analog 1 (Sequence I.D. No.1):

Derived from Alpha Chemokine - IL-8 (also called NAP-1)
Glu—Leu—Arg—Cys—Gln—Cys—Ile—Lys—Thr—Tyr—Ser—Lys—Pro—Phe—His—Pro—Lys Analog 2 (Sequence I.D. No. 2):

Derived from Alpha Chemokine - IL-8 (also called NAP-1)
Glu—Leu—Arg—Cys—Gln—Cys—Ile—Lys—Thr—Tyr—Ser—Lys—Pro—Phe Analog 3 (Sequence I.D. No.3):

Derived from Alpha Chemokine - GRO-α (also called MGSA)
Glu—Leu—Arg—Cys—Gln—Cys—Leu—Gln—Thr—Leu—Gln—Gly—Ile—His—Pro—Lys Analog 4 (Sequence I.D. No.4):

Derived from Alpha Chemokine - GRO-β (also called MIP-2σ)
Glu—Leu—Arg—Cys—Gln—Cys—Leu—Gln—Thr—Leu—Gln—Gly—Ile—His—Leu—Lys Analog 5 (Sequence I.D. No. 5):

Derived from Alpha Chemokine - GRO
Glu—Leu—Arg—Cys—Gln—Cys—Leu—Gln—Thr—Met—Thr—Gly—Val—His—Leu—Lys Analog 6 (Sequence I.D. No. 6):

Derived from Alpha Chemokine - GRO-g (also called MIP-2β)
Glu—Leu—Arg—Cys—Gln—Cys—Leu—Gln—Thr—Leu—Gln—Gly—His—Leu—Lys Analog 7 (Sequence I.D. No. 7):

Derived from Alpha Chemokine-β thromboglobulin (also called NAP-2)
Glu—Leu—Arg—Cys—Met—Cys—Ile—Lys—Thr—Thr—Ser—Gly—Ile—His—Pro—Lys Analog 8 (Sequence I.D. No. 8):

Derived from Alpha Chemokine - 9E3
Glu—Leu—Arg—Cys—Gln—Cys—Ile—Ser—Thr—His—Ser—Lys—Phe—Ile—His—Pro—Lys Analog 9 (Sequence I.D. No. 9)

Derived from Alpha Chemokine - 310C
Glu—Leu—Arg—Cys—Gln—Cys—Ile—Lys—Thr—Tyr—Ser—Lys—Pro—Phe—His—Pro—His Analog 10 (Sequence I.D. No. 10):

Derived from Alpha Chemokine - CNC
Glu—Leu—Arg—Cys—Gln—Cys—Leu—Gln—Thr—Val—Ala—Gly—Ile—His—Phe—Lys Analog 11 (Sequence I.D. No. 11):

Derived from Alpha Chemokine - ENA-78
Glu—Leu—Arg—Cys—Val—Cys—Leu—Gln—Thr—Thr—Gln—Gly—Val—His—Pro—Lys The present invention includes analogs that are essentially equivalent to any analog of the invention, as specified in Table 2. An analog is essentially equivalent to one specified above if it has one or more of the biological activities characteristic of human IL-8, essentially has the same number of amino acids as the analog specified in Table 2 with no more than two additions or deletions and, in comparison with the sequence of the specified analog, has at most five amino acid substitutions, all of which would be considered neutral in the art (i.e., acidic for acidic, basic for basic, uncharged polar for uncharged polar, hydrophobic for hydrophobic, and the like).

The acidic amino acids are Asp, Glu and gammacarboxyglutamic acid. The basic amino acids are Arg, Lys, His and Orn. The hydrophobic amino acids are Ala Ile, Leu, Met, Nor, Phe, Trp, Tyr, Val, t-butylglycine, norvaline, cyclohexylalanine, t-butylalanine, amino-4-phenylbutyric acid, beta-2-thienylalanine, p-bromophenylalanine, p-chlorophenylalanine, p-iodophenylalanine, p-nitrophenylalanine, 3.5-diiodotyrosine, phenylglycine, and napthylalanine. Uncharged polar amino acids are Asn, Gln, Ser, and Thr. Gly can be substituted for an uncharged polar or a hydrophobic amino acid, but substitutions with Pro are avoided because helical structures may be destabilized by such a significant effect on secondary structure of inserting a Pro in place of another amino acid.

Substitutions with Cys are specified and may include substitution with α-aminobutyric acid (Aba). This nonnatural amino acid is suggested to cause a super-imposition with cysteine. Its ethyl side chain is closer to being isosteric than any of the naturally occurring non-polar amino acids. In addition, it is specified that it can be substituted with homocysteine or diaminosuberic acid replacing the cysteines thereby retaining charge and size conformation but in the absence of homodimerization.

The chiral amino acids of the IL-8 analogs of the present invention have the L configuration.

Analog 1 was designed as a structural mimic of IL-8 from amino acid residues 4 to 20. Analog 1 contains overall homology with the amino acid sequence of human IL-8.

Analog 2 was designated as a structural mimic of human IL-8 from amino acid residues 4 to 17. Analog 2 has been C-terminally truncated compared to analog 1, with slight loss of activity, compared to analog 1.

An analog of the present invention can be made by exclusively solid phase techniques, by partial solid-phase techniques, by fragment condensation, by classical solution coupling, or, as long as the analog consists of only amino acids among the twenty naturally occurring amino acids corresponding to codons of the genetic code, by employing recombinant DNA techniques with bacteria, such as *E.coli* or *B. subtilis*; yeast, such as *S. cerevisiae* or *P.pastoris*; or insect or mammalian cells.

Methods of making a polypeptide of known sequence by recombinant DNA techniques are well-known in the art. See, e.g., U.S. Pat. No. 4,689,318, which is incorporated herein by reference.

Methods for chemical synthesis of polypeptides are also well-known in the art and, in this regard, reference is made, by way of illustration, to the following literature: Yamashino and Li, J Am Chem Soc 100:5174–5178, 1978; Stewart and Young, Solid Phase Peptide Synthesis (W H Freeman and Co. 1969); Brown et al., J C S Perkin I, 1983, 1161–1167; M. Bodanszky et al., Bioorg Chem 2:354–362, 1973; U.S. Pat. Nos. 4,689,318; 4,632,211; 4,237,046; 4,105,603; 3,842,067; and 3,862,925, all of which are incorporated herein by reference.

Preferred, automated, step-wise solid-phase methods for synthesis of peptides of the invention are provided in the examples below.

The IL-8 analogs encompassed by the present invention have one or more of the biological activities of naturally occurring IL-8, as described above, and, as such, are useful therapeutically in one or more of the ways in which IL-8 is known to be useful, e.g., as an anti-infective for bacterial, fungal, viral, and or protozoan infections, as an antineoplastic for both leukemia, solid and metastatic disease.

The biological activity of an analog of the invention is determined by comparing the analog with naturally occurring IL-8.

The analogs of the invention are employed therapeutically, under the guidance of a physician for the treatment of leukemic or solid tumors or metastatic disease and infectious diseases including but not limited to viral, bacterial, fungal, yeast or parasitic.

The dose and dosage regiment of an analog according to the invention that is suitable for administration to a particular patient can be determined by a physician considering the patient's age, sex, weight, general medical condition, and the specific condition and severity thereof for which the analog is being administered; the route of administration of the analog; the pharmaceutical carrier with which the analog may be combined; and the analog's biological activity, relative to that of naturally occurring human IL-8, in the above-described assays.

Generally, intravenous injection of 1–500 μmol of analog/kg body weight, by bolus injection, by infusion over a period of about 5 minutes to about 60 minutes, or by continuous infusion is sufficient for therapeutic efficacy. Aerosol inhalation of 0.1 or 2 mg of analog/kg body weight is also sufficient for efficacy.

Intravenous, subcutaneous or intramuscular administration, by bolus injection or continuous infusion, is preferred for use of the analogs of the invention in treatment of neoplastic or infectious disease.

The analogs of the invention, or a pharmaceutically acceptable salt thereof, can be combined, over a wide concentration range (e.g., 0.001 to 11.0 wt %) with any standard pharmaceutical carrier (e.g., physiological saline, THAM solution, or the like) to facilitate administration by any of various routes including intravenous, subcutaneous, intramuscular, oral, or intranasal, including by inhalation.

Pharmaceutically acceptable acid addition salts of the analogs of the invention can be prepared with any of a variety of inorganic or organic acids, such as for example, sulfuric, phosphoric, hydrochloric, hydrobromic, nitric, citric, succinic, acetic, benzoic and ascorbic. The analogs can, for example, be advantageously converted to the acetate salt by dissolution in an aqueous acetic acid solution (e.g., 10% solution) followed by lyophilization.

Pharmaceutical compositions containing a compound of the present invention as the active ingredient in intimate admixture with a pharmaceutical carrier can be prepared according to conventional pharmaceutical compounding techniques. The carrier may take a wide variety of forms depending on the form of preparation desired for administration, e.g., intravenous, oral or parenteral. In preparing the compositions in oral dosage form, any of the usual pharmaceutical media may be employed, such as, for example, water, glycols, oils, alcohols, flavoring agents, preservatives, coloring agents and the like in the case of oral liquid preparations (such as, for example, suspensions, elixirs and solutions); or carriers such as starches, sugars, diluents, granulating agents, lubricants, binders, disintegrating agents and the like in the case of oral solid preparations (such as, for example, powders, capsules and tablets). Because of their ease in administration, tablets and capsules represent the most advantageous oral dosage unit form in which case solid pharmaceutical carriers are obviously employed. If desired, tablets may be sugar-coated or enteric-coated by standard techniques. For parenterals, the carrier will usually comprise sterile water, though other ingredients, for example, to aid solubility or for preservative purposes, may be included. Injectable suspensions may also be prepared, in which case appropriate liquid carriers, suspending agents and the like may be employed. The pharmaceutical compositions will generally contain dosage units, e.g., tablet, capsule, powder, injection, teaspoonful and the like, from about 0.001 to about 10 mg/kg, and preferably from about 0.01 to about 0.1 mg/kg of the active ingredient.

The following examples are provided to further illustrate the present invention and are not intended to limit the invention beyond the limitations set forth in the appended claims.

EXAMPLE 1

Peptides were synthesized using solid-phase methodology, generally described by Merrifield (J Amer Chem Soc 85:2149, 1963) (see also Stewart and Young, supra) with various modifications described herein, carried out on an Applied Biosystems 431A automated peptide synthesizer (Applied Biosystems, Foster City, Calif. USA).

Sequential assembly of a peptide analogue is conducted from the carboxy-terminus, bonded to a solid-phase resin, to the amino terminus; the addition of amino acids to a peptide chain is automated after the attachment of the carboxy-terminal amino acid to the resin.

For peptides that will have a carboxyl group at the carboxy-terminus, p-chloromethyl-derivatized polystyrene supports are employed, and the carboxy-terminal amino acid is esterified to the support via reaction with KF as described by Horiki et al., Chem Lett 1978, 165–168. Analogs with a C-terminal proline or a penultimate C-terminal proline may be synthesized using a 2-chlorotrityl chloride derivatized resin. Attachment of FMOC amino acids to the resin can be quantitated by spectrophotometric determination at 266 nm following treatment of a weighed sample with 50% piperidine in DMF. Substitution levels for automated syntheses are preferably between 0.2 and 0.6 mmol amino acid per g resin. A typical FMOC synthesis is performed on a scale of 0.1–0.25 mmol and thus is initiated with 0.15–1.25 g amino acid-derivatized resin. Steps in the syntheses of the IL-8 analogs employed the following Protocol I(a):

| Step | Reagent | Mix Time (min) | # of Times |
|---|---|---|---|
| 1 | 20% piperidine in NMP | 16.4 | 2 |
| 2 | 0.45M HBTU/HOBT in DMF/in NMP | 7.6 | 1 |
| 3 | NMP | 4.6 | 1 |
| 4 | 2.0M DIEA in NMP | 2.2 | 1 |
| 5 | NMP | 22.2 | 1 |
| 6 | 0.5M acetic anhydride/0.125M DIEA/0.015M HOBT/in NMP | 6.4 | 1 |
| 7 | NMP | 4.6 | 1 |
| 8 | Stop or return to step 1 for next coupling | | |

NMP = N-Methylpyrrolidone
HBTU = 2-(1H-benzotriazol-1-yl)-1,1,3,3-tetramethyluronium hexafluorophosphate
HOBT = 1-Hydroxybenzotriazole
DMF = Dimethylformamide
DIEA = Diisopropylethylamine All chemicals were reagent or peptide synthesis grade and were used as purchased. DIEA and NMP were from Fisher Scientific, Fair Lawn, N.J., USA. Piperidine, HOBT and HBTU were from Advanced ChemTech, Louisville, Ky., USA. DMF was from E. Merck, Gibbstown, N.J., USA,. Acetic anhydride was from FLUKA, Buchs, Switzerland. The coupling of amino acids was carried out for 45 minutes with a four-fold excess of the activated esters of the FMOC amino acids with respect to the available amine sites on the resin.

The 9-Fluorenyl methoxycarbonyl (FMOC) group was used for protection of the alpha amine group of all amino acids employed in the syntheses; however, other protecting groups known in the art for alpha amines can be employed successfully. Side-chain functionalities were protected as follows: Arg with 4-Phenylazobenzyloxycarbonyl; Cys, Gln, and His with trityl; Glu, Ser, and Thr with benzyl; Lys with tertiary butyloxycarbonyl; and Tyr with tertiary butyl.

Resins employed in the syntheses were purchased with the C-terminal residue already attached to derivatized polystyrene-1% divinyl-benzene (200–400 mesh), either by 4-hydroxymethylphenoxyacetic acid or 2-chlorotrityl chloride.

After assembly of the completed analog, the amino-terminal FMOC group is removed using step 1 of the above protocol and then the resin is washed with methylene chloride and dried. The analogs are then deprotected and removed from the resin support by treatment with TFA for 2 hours at 25 degree(s) C. The peptide is precipitated with cold diethyl ether, the liquid phase is filtered away and the peptide is extracted with 10% acetic acid in water and lyophilized.

The resulting crude preparations were purified by preparative high performance liquid chromatography (HPLC) on a Waters C-18 column (40×200 mm) (Millipore Corp, Millford, Mass., USA) and analyzed by analytical HPLC. Preparative HPLC separations were performed with the Waters column on a Waters Delta Prep 4000 System (Millipore Corp, Millford, Mass., USA) at a flow rate of 75 ml/min. Samples were introduced in 0.1% TFA (running buffer) and after a 5 minute lag to ensure complete loading, eluted from the column with a 1%/minute acetonitrile gradient with an elution time of 24–26 minutes. Peptide fractions were monitored by UV absorbance at 220 nm. In all cases, fractions were manually collected at peak detection. The purified fractions were analyzed on an analytical HPLC System, Waters 712 WISP, using a Waters C-18 column (8×100 mm) using 0.1% TFA and an acetonitrile gradient. Other HPLC buffer systems which may be employed in the analytical HPLC include triethylamine phosphate (TEAP), pH 2.5–3.0, TEAP, pH 6.5, and a mixture of 0.1% phosphoric acid, 0.1M sodium perchlorate, pH 2.5 with an acetonitrile gradient. Although the TFA buffer system does not resolve microheterogeneous contaminants as well as other systems, recovery is generally 50–90% higher. A portion of a fraction from the preparative HPLC which appeared homogenous by analytical HPLC was removed, lyophilized and hydrolyzed for amino acid analysis. These portions with the proper amino acid compositions and proper mass, determined by matrix assisted laser desorption ionization—time of flight (MALDI-TOF) mass spectometry, were treated to replace the TFA with acetic acid and were then subjected to bioassay.

For amino acid analysis, a sample of analog was hydrolyzed in 6N HCI containing 1% phenol for 70 minutes at 110 degrees C. Analyses were performed by a procedure which is a modification of the method of Cohen and Michaud (Anal. Biochem 211:279–287, 1993) employing the AccQ Tag reagent (Waters, Millford, Mass., USA).

(a) SYNTHESIS OF THE IL-8

The synthesis of Analog 1, IL-8, was initiated by using 581 mg of an H-LYS(BOC) 2-chlorotrityl resin (substitution level=0.43 mmol/g), purchased from AnaSpec, Inc., (San Jose, Calif., USA). The synthesis was carried out automatically by the ABI 431A Peptide Synthesizer. The amount of components is summarized in the following Table 1(b):

| CYCLE | Grams/protected amino acid |
|---|---|
| 1 | .337 P |
| 2 | .620 H |
| 3 | .387 F |
| 4 | .337 P |
| 5 | .469 K |
| 6 | .327 S |

-continued

| CYCLE | Grams/protected amino acid |
|---|---|
| 7 | .494 Y |
| 8 | .341 T |
| 9 | .469 K |
| 10 | .353 I |
| 11 | .586 C |
| 12 | .612 Q |
| 13 | .586 C |
| 14 | .397 R |

Upon completion of the synthesis, 1.2 g of peptide-resin was obtained. This was added to 10 ml of TFA in a 100 ml round bottom flask with 500 μl of $H_2O$, 500 μl thioanisole, 250 μl ethanedithiol and 750 mg phenol and stirred at 25 degree(s) C. for 2 hours. The reaction was terminated by the addition of 100 ml cold diethyl ether to precipitate the peptide. The solution was filtered and the peptide was extracted with 100 ml 10% acetic acid in water, frozen, and lyophilized. A small portion was dissolved in 225 μl of 0.1% TFA and injected onto the analytical HPLC using the previously described conditions to determine elution characteristics for the preparative scale purification. The remainder of the crude peptide was loaded onto the preparative system and eluted under the above conditions. A 0–40% acetonitrile gradient over 40 minutes was used to elute the peptide components. An aliquot of homogeneous fractions from preparative HPLC was removed, and then hydrolyzed for amino acid analysis. Amino acid analysis results: Ser (1)0.96, Glx (2)1.98, His (1)1.04, Thr (1)0.94, Arg (1)1.08, Pro (2)1.82, Cys (2)1.86, Tyr (1)1.07, Lys (3)2.94, Ile (1)1.13, Phe (1)1.14, and Leu (1)0.98. The MALDI-TOF mass spectrum showed the proper mass peak and only peptide-matrix peaks. Amino acid analysis of a weighed sample showed the powder to be 85.9% peptide by mass.

EXAMPLE II

In Vivo Bioreactivity Assay of IL-8 Analogs

A stock solution of 5 mg/ml of analog 1 was prepared using Dulbecco's phosphate buffered saline D-PBS. The solution was made 5× to compensate for the injection of 0.2 ml ip. The mice were dosed at various times with various doses of Analog 1. The ip administration was with a volume of 0.2 ml. In addition, excipient control animals were injected.

The mice used for the study were C57BL/6 females, which were obtained from Jackson Laboratories. The mice used in these studies were at 8–10 weeks of age and weighed 15–18 g. The mice were housed in conventional cages, fed pelleted food and given water ad libitum.

At various times following injection of Analog 1 the mice were bled from retinal orbital plexus with 40 μl removed into heparanized capillary tubes and the blood analyzed using a Serona Baker 9000 Blood analyzer. In addition, blood films were made and differentials undertaken on at least 200 cells/sample.

The mice were sacrificed by ether overdose, the ventral skin reflected and the peritoneum lavaged with three 5 ml lavages of calcium-, magnesium- free HBSS. At one, two, four, eight and 24 hours, following injection, three to five mice and/or control mice were lavaged and the cells collected in 15 ml tubes. The peritoneal cells were then centrifuged and counted. In addition, a differential was done on the peritoneal cells in a cytospin preparation. For the cytospin, 25 μl of bovine albumin (Sigma Lot #70H0183) was first placed in the bottom of the chamber, and 100 μl of cell suspension (100,000 cells) added. It was spun at 1000 rpm for 5 minutes and then left to dry. Next, they were placed in leukostat fixative solution for 5 seconds followed by 45 seconds in Leukostat solution 1 and 45 seconds in Leukostat solution 2 and finally washed in deionized $H_2O$ for 5 seconds and allowed to dry. The slides were analyzed under microscope for differentials.

EXAMPLE III

In Vitro BioAssay of IL-8 Analogs

Cell Preparation—Polymorphonuclear leukocytes (≧95% neutrophils, PMNs) were isolated from heparinized (10U/ ml) blood collected from healthy volunteers. Erythrocytes were removed by 6% dextran sedimentation for 30 minutes at room temperature, and then the supernatant was subjected to Ficoll (Ficoll-Paque, Pharmacia LKB, Uppsala, Sweden) density gradient centrifugation. PMNs were obtained from the pellet. Contaminated erythrocytes were eliminated by one cycle of hypotonic lysis. After an additional washing step the cells were counted and adjusted to a final concentration of $5 \times 10^6$/ml in RPMI 1640 (Gibco, Grand Island, N.Y.).

Fluo-3 Loading—The loading procedure with Fluo-3 (Molecular Probes, Eugene, Oreg.) was carried out with PMNs suspended at a density of $5 \times 10^6$/ml in fresh RPMI 1640 containing 2.0 μM Fluo-3 AM (prediluted in dimethyl sulfoxide; Sigma Chemicals) in polypropylene tubes (Falcon 2063, Becton Dickinson). We incubated the PMNs for 25 minutes at 37 degrees C. in a 5% $CO_2$ incubator. During the incubation period the PMNs were gently agitated twice. To remove extracellular Fluo-3 AM, cells were washed twice with RPMI 1640 and with $Ca_{2+}$ and $Mg_{2+}$— free phosphate-buffered saline (PBS) containing 100 mM KCl and 5 mM HEPES buffer at pH 7.05. Finally, the cells were adjusted to a density of $5 \times 10^5$/100 μl in the PBS buffer and suspended in 5×35 mm tubes. The samples were kept in the dark at room temperature until use.

Measurement of $[Ca^{2+}]$ in Flow Cytometry—Before addition of the stimuli the fluorescence channel of the FACScan Plus (Becton Dickinson) was adjusted to find the basal fluorescence level of loaded but unstimulated PMNs. The samples were excited by an argon laser at 488 nm and emission was measured at 525 nm (green fluorescence, channel FL1). The temperature has no effect on the appearance of neutrophil subpopulations with different $[Ca^{2+}]$ mobilizations. However, the experiments were carried out at room temperature (22 degrees C.). PMNs were then stimulated at different concentrations with IL-8/NAP-1 or experimental analogs. The events were acquired before and 5 s after addition of the stimuli, and acquisition was continued over 80 s. For each acquisition 2500–3000 events were collected in 6 s interrupted for a time interval of 8 s or less using the FACScan software (Becton Dickinson). The fluorescence of Fluo-3-loaded cells was measured in arbitrary fluorescence units of mean channel fluorescence (channel FL1). To control the influence of the medium, PBS (supplemented as described above) was added instead of stimuli. A continuous measurement of unstimulated PMNs was also carried out. Both procedures did not result in an increase in arbitrary fluorescence units.

EXAMPLE IV

In Vivo Activity of Analog I

Figure 2:
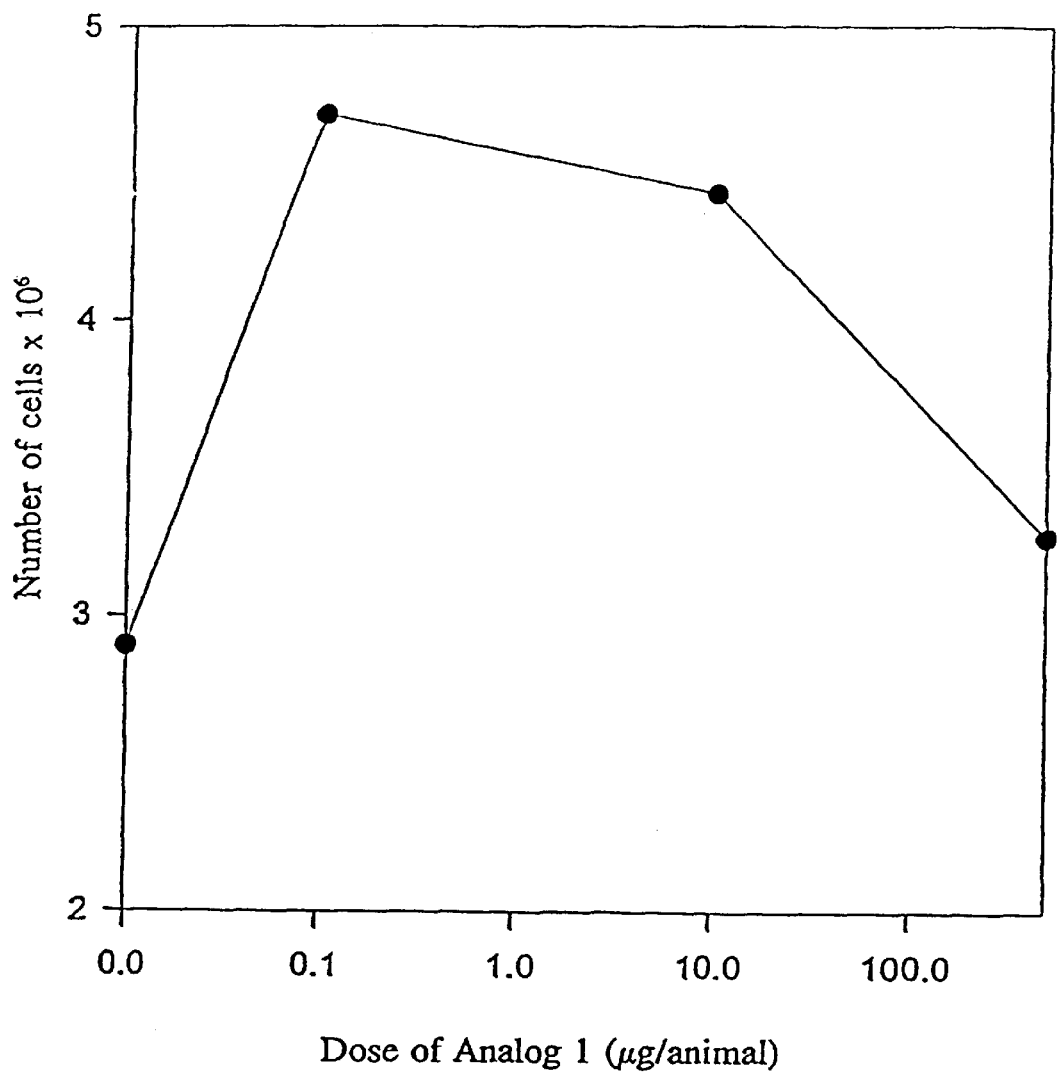
FIG. 2: A graph of a dose response curve showing the chemotactic effects of a single i.p. injection of Analog 1 in increasing concentrations. X axis represents the dose of Analog 1 in μg/animal. Y axis depicts cell number×$10^6$ in the peripheral blood.
Figure 3:
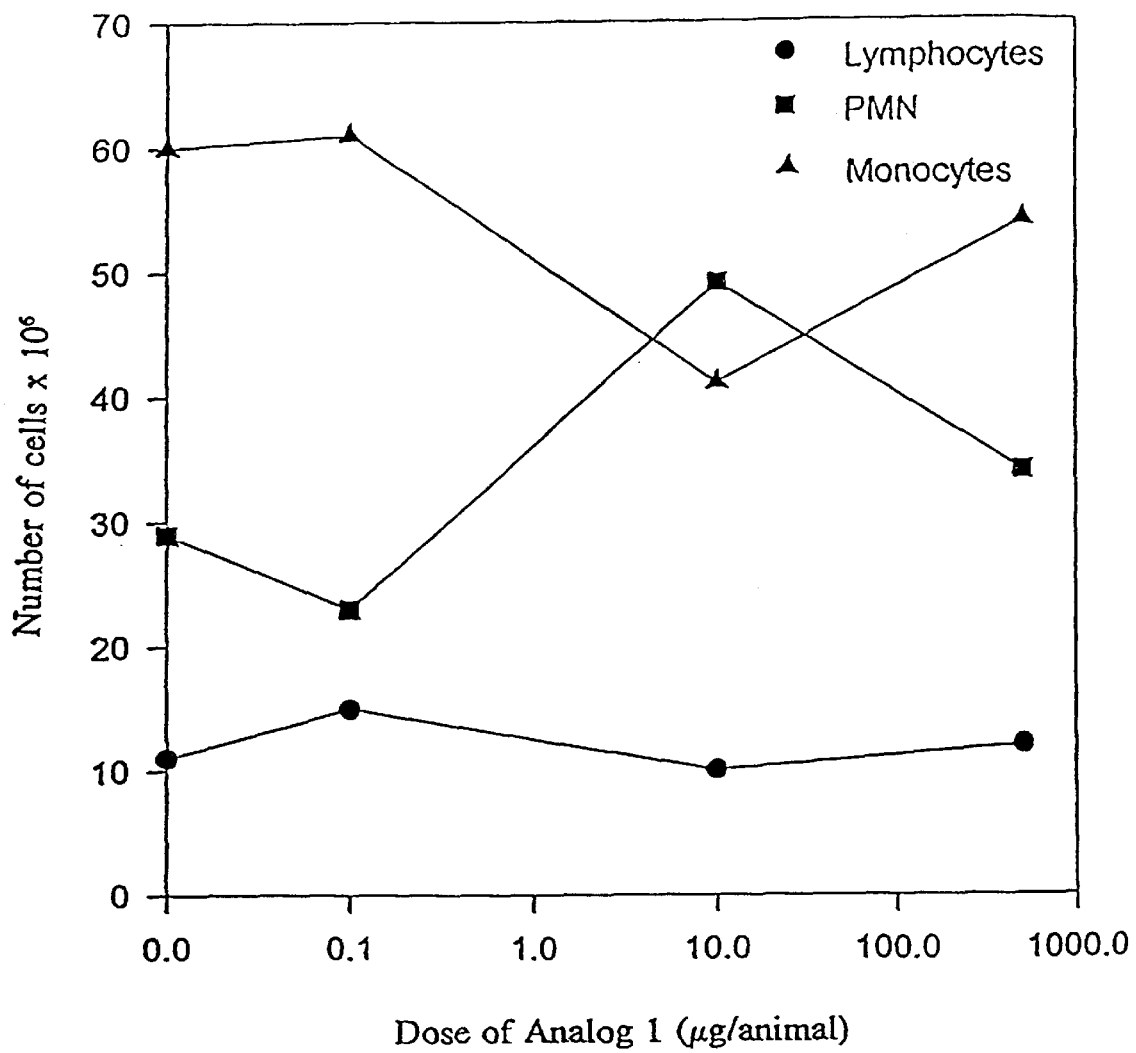
FIG. 3: A graph showing the different cell types present in the peritoneum in response to increasing amount of i.p. injected Analog 1. The X axis represents the dose of Analog 1 in μg/animal; The Y axis represents cell number×$10^6$ in the peritoneum. ●lymphocytes; ■PMNs; ▲ monocytes.
Figure 4:
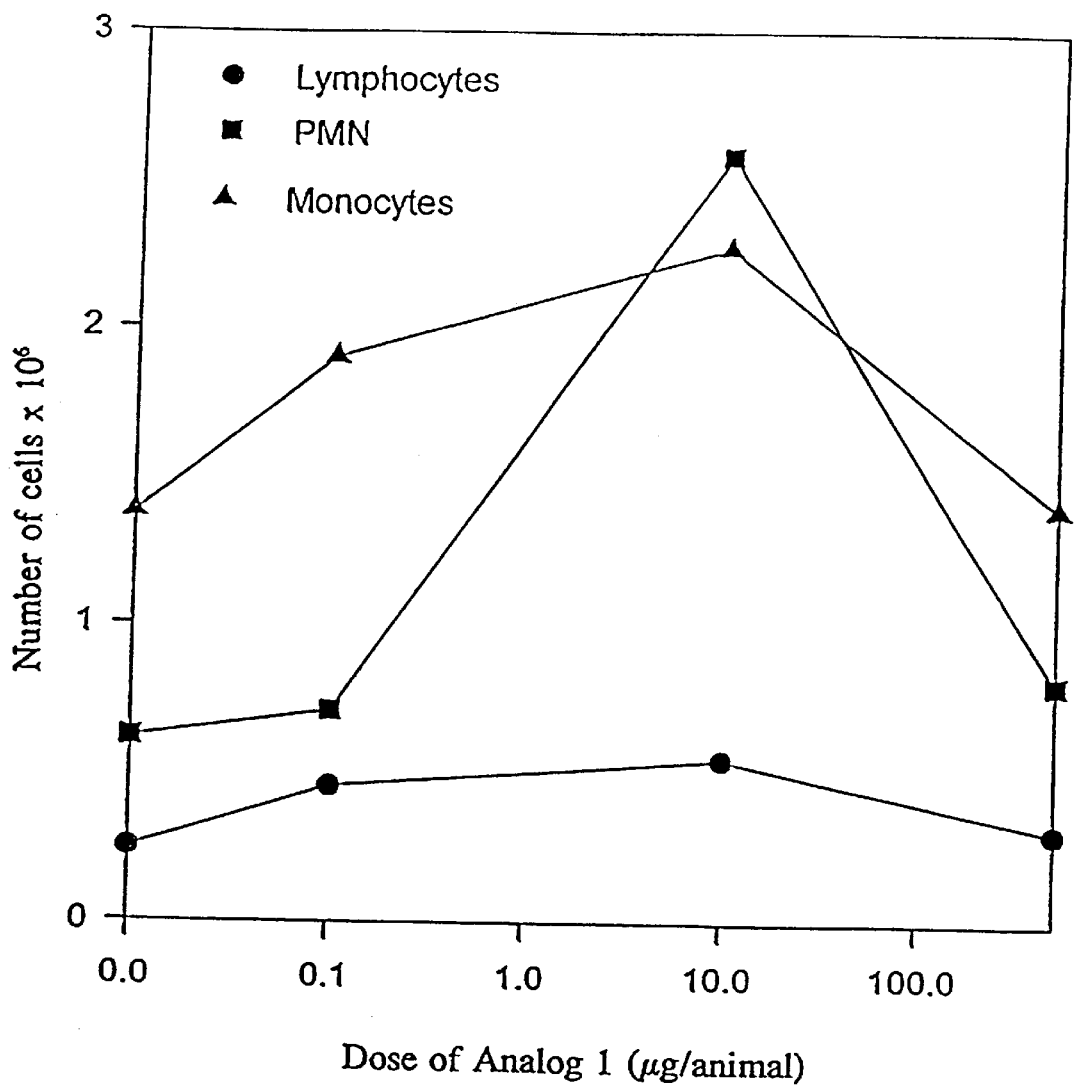
FIG. 4: A graph showing the absolute cell number of different cell types present in the peritoneum after an i.p. injection of Analog 1. The X axis represents the dose of Analog 1 in μg/animal; The Y axis represents cell number× $10^6$ in the peritoneum. ●lymphocytes; ■PMNs; ▲ monocytes.
Figure 5:
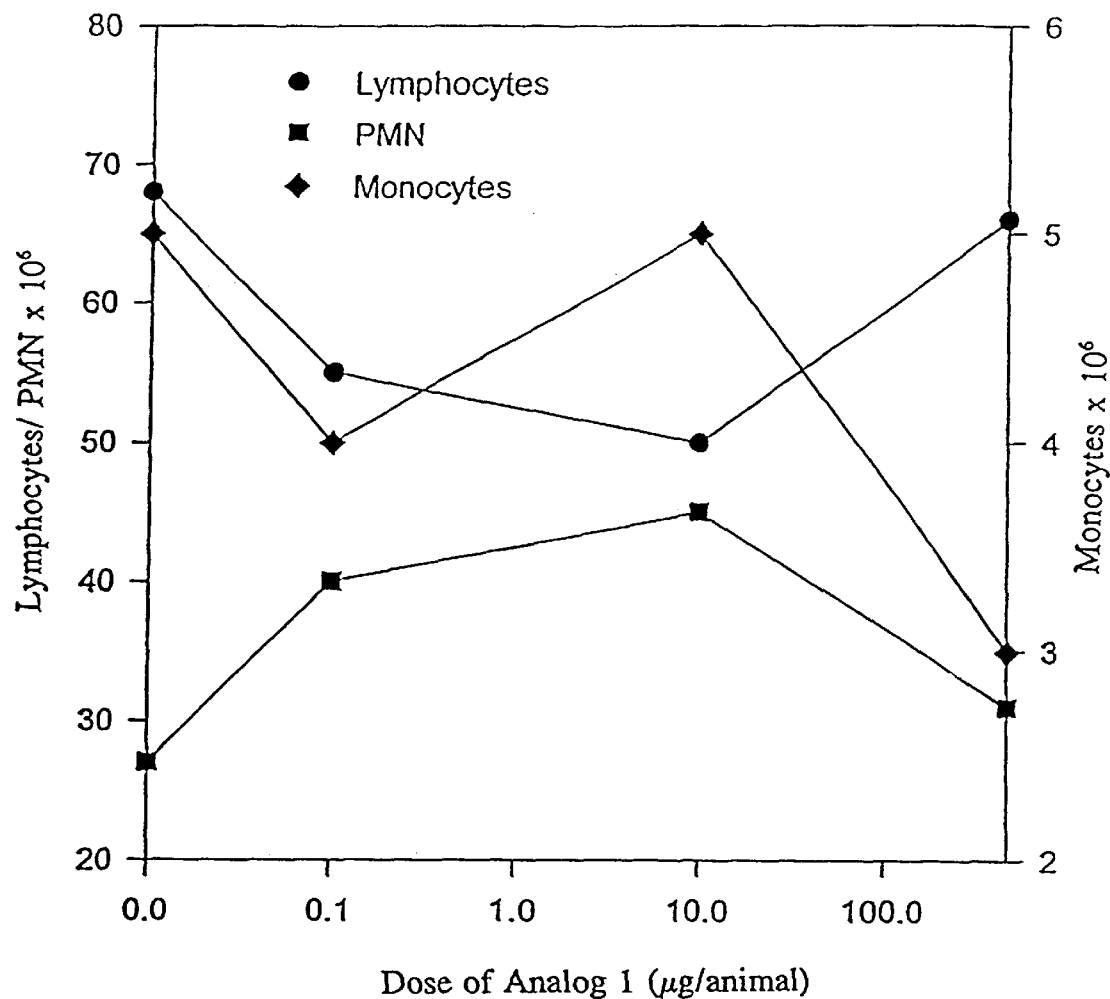
FIG. 5: A graph showing the different cell types present in the peripheral blood after a single i.p. injection of Analog 1. The X axis represents the dose of Analog 1 in μg/animal. The ratio of lymphocytes to PMNs is shown on axis Y1; the number of monocytes is shown on Y2. ●lymphocytes; ■PMNs; ♦ monocytes.
Figure 6:
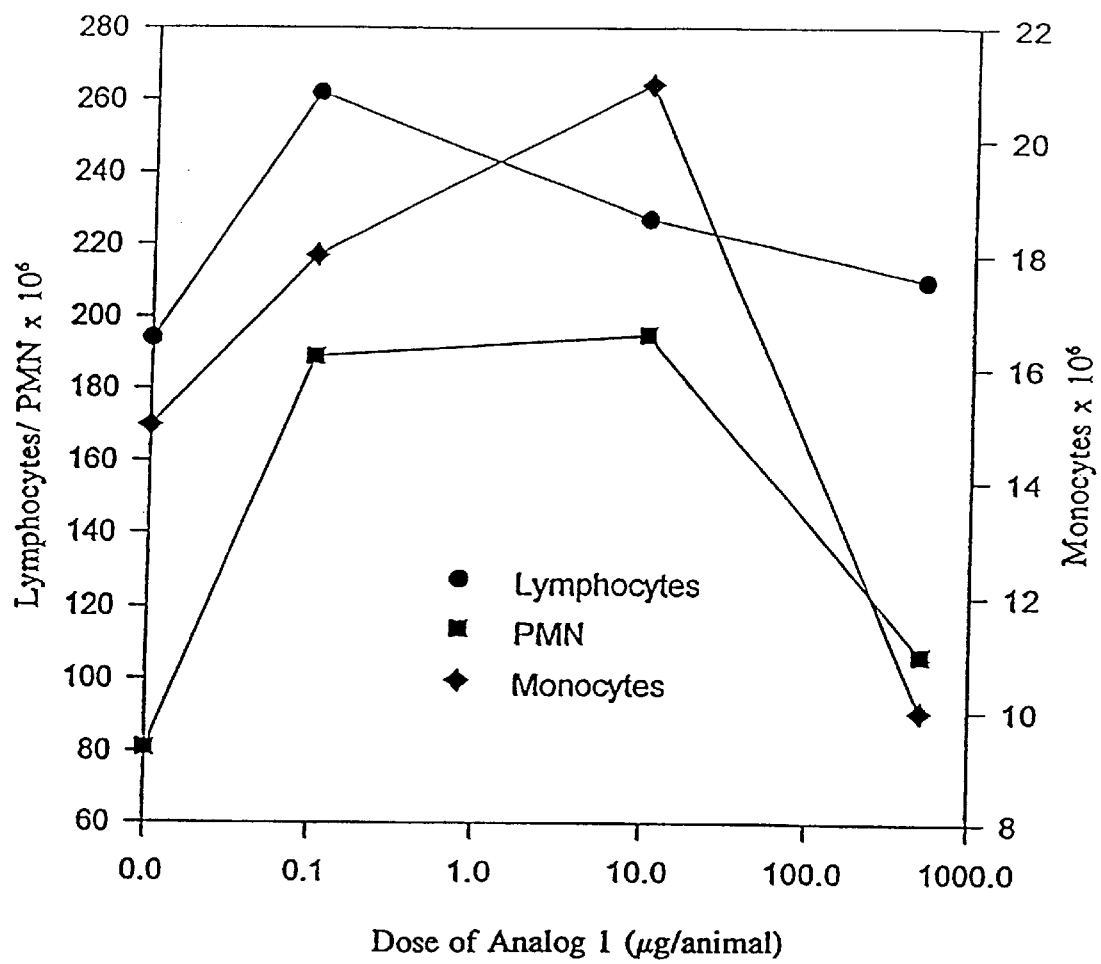
FIG. 6: A graph showing the absolute cell number of different cell types present in the peripheral blood after a single i.p. injection of Analog 1. The X axis represents the dose of Analog 1 in μg/animal. The ratio of lymphocytes to PMNs is shown on axis Y1; the number of monocytes is shown on Y2. ●lymphocytes; ■PMNs; ♦ monocytes.

A low molecular weight peptide analog of IL-8 showed biological activity in in vivo assays according to the methods described in Example II. The in vivo chemotactic activity of Analog 1 for cells into both the peritoneum and PBL are shown herein. FIG. 1 shows the effect of a single ip injection of this low molecular weight peptide analog on peritoneal cellularity when employed in increasing concentrations from 0.1–500 μg/animal. Optimal activity was observed at 10 μg/animal. Similarly, a significant increase in PBL cellularity (FIG. 2) was observed with maximal activity at 0.1 and 10 μg/animal. The primary cell type elicited in the peritoneum by the ip injection of this low molecular weight peptide analog was PMNs as shown in FIG. 3. This resulted in a four-fold increase in PMN into the peritoneum and almost a two-fold increase in monocyte/macrophages into the peritoneum (FIG. 4). Similarly, there was an increase in the frequency of PMNs in the peripheral blood (FIG. 5) and a significant increase in the absolute number of PMNs and monocytes in the peripheral blood (FIG. 6).

Figure 7:
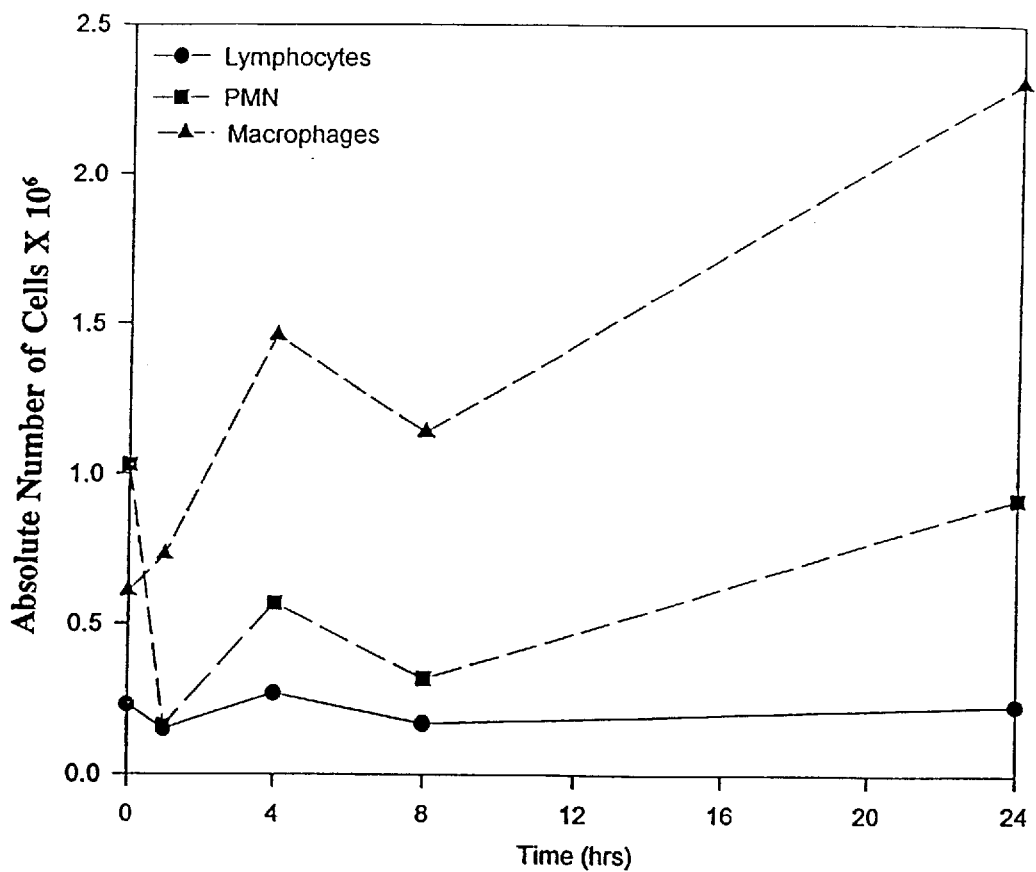
FIG. 7: A graph showing the kinetics of the in vivo chemotactic response in the peritoneum following an i.p. injection of 10 μg of Analog 1. The X axis represents time in hours and the Y axis represents the absolute cell number. ●lymphocytes; ■PMNs; ♦ macrophages.

Low molecular weight peptide analogs having residues 4–20 were synthesized according to the method described herein (Example 1). FIG. 7 shows the kinetics of the in vivo chemotactic response in the peritoneum following ip injection of 10 μg of this peptidal low molecular weight analog. The greatest increase observed was in the number of macrophages and PMNs in the peritoneum.

These results are substantially identical to nonhuman primate studies which demonstrated the hematologic effects of IL-8 following parenteral administration. IL-8 was administered by both push and continuous infusion to baboons. This resulted in a granulocytosis which persisted as long as IL-8 remained detectable within the circulation (Van Zee, K. J. et al., J Immunol, 1992, 148:1746–1752). Similar results have been observed in a rabbit where natural IL-8 was injected intradermally in the presence of a vasodilator substance. In these studies, IL-8 induced a neutrophil accumulation that was fast in onset, relatively short in duration and was associated with a parallel time course of plasma protein extravasation (Rampart, M., A J Pathol, 1989, 135:21–25).

EXAMPLE V

Figure 8A:
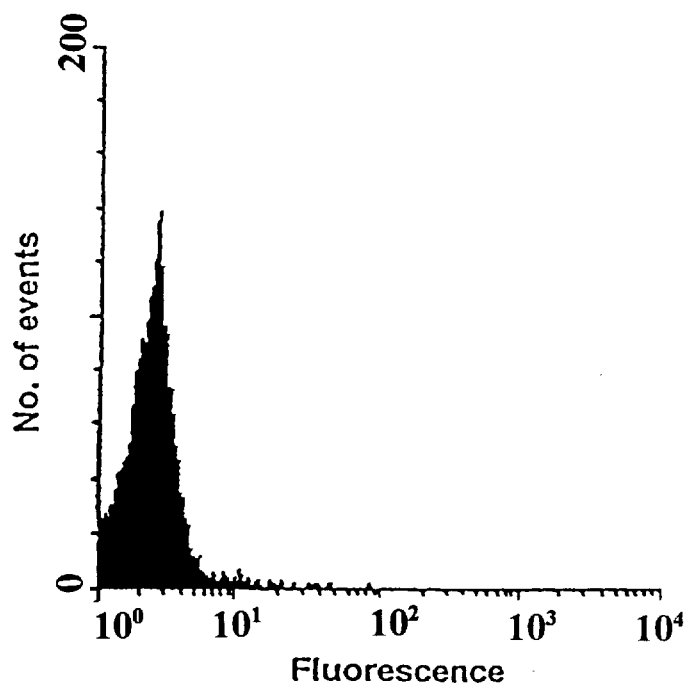
FIGS. 8A and 8B: FACS analysis profiles a $Ca^+$ release from polymorphonuclear monocyts (PMNs), unstimulated (FIG. 8A) or stimulated with native IL-8 (FIG. 8B).
Figure 8B:
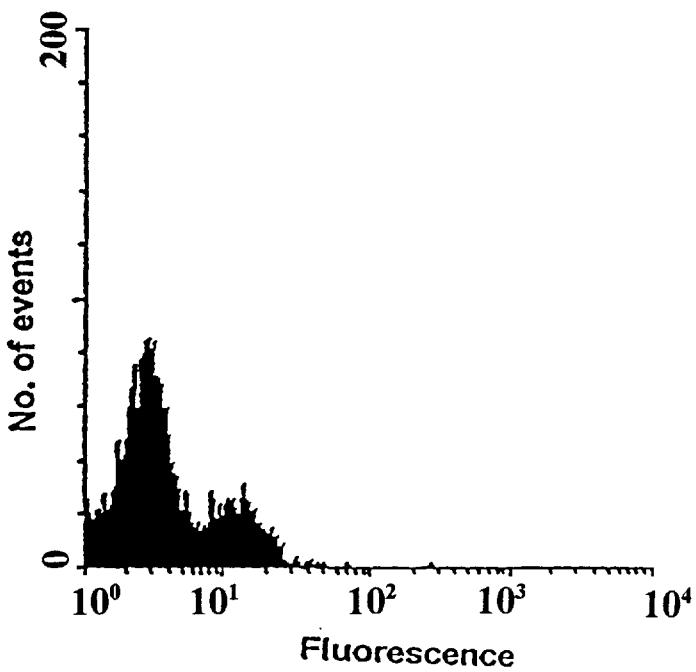
Figure 9A:
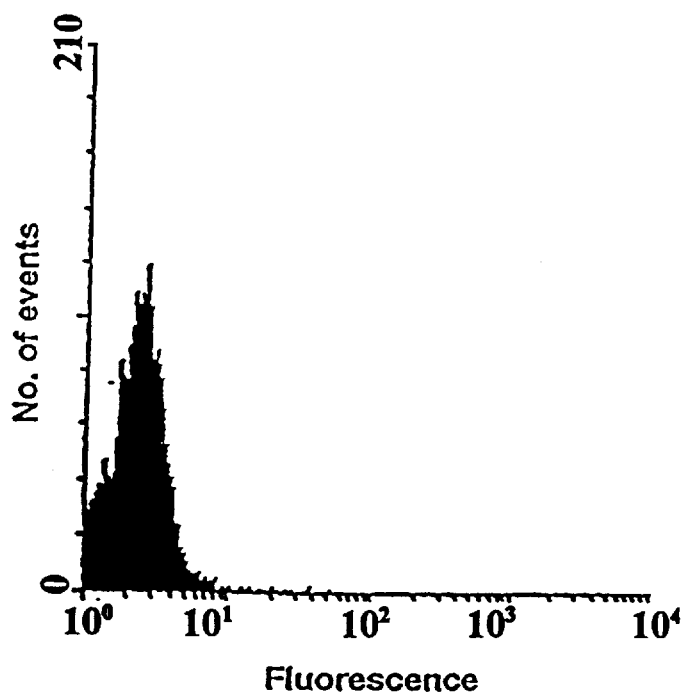
FIGS. 9A and 9B: FACS analysis profiles a $Ca^+$ release from untreated (FIG. 9A) and PBS treated (FIG. 9B) PMNs.
Figure 9B:
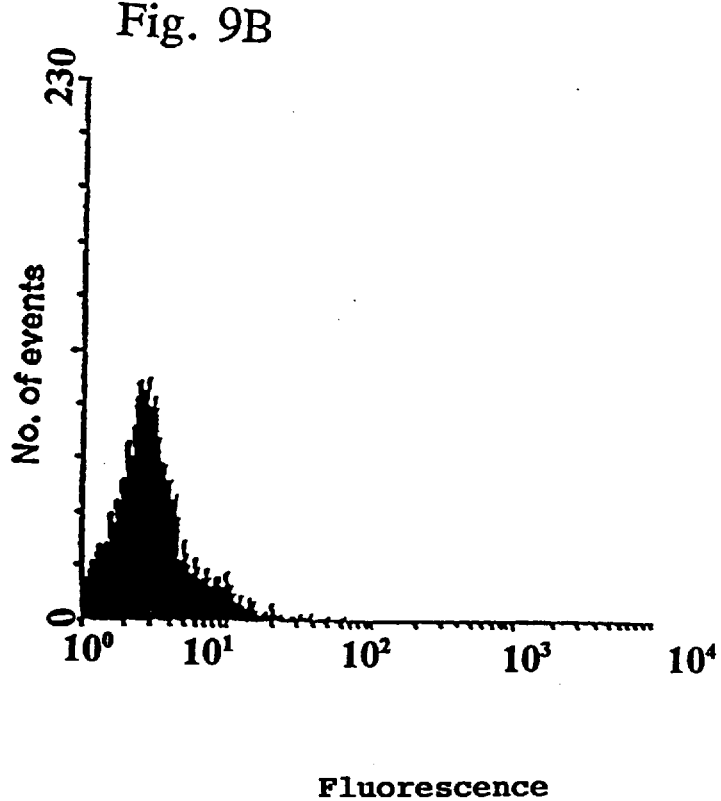
Figure 10A:
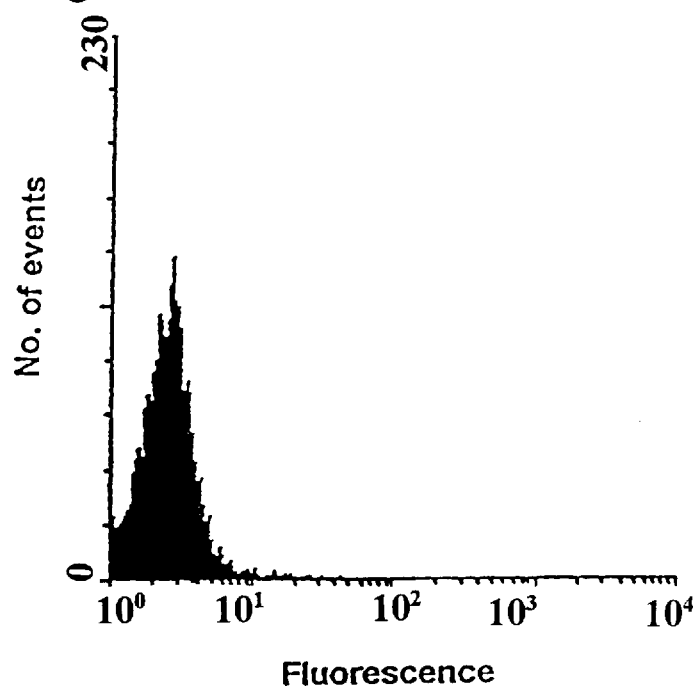
FIGS. 10A and 10B: FACS analysis profiles a $Ca^+$ release from untreated (FIG. 9A) and Analog 1 treated PMNs (FIG. 10B).
Figure 10B:
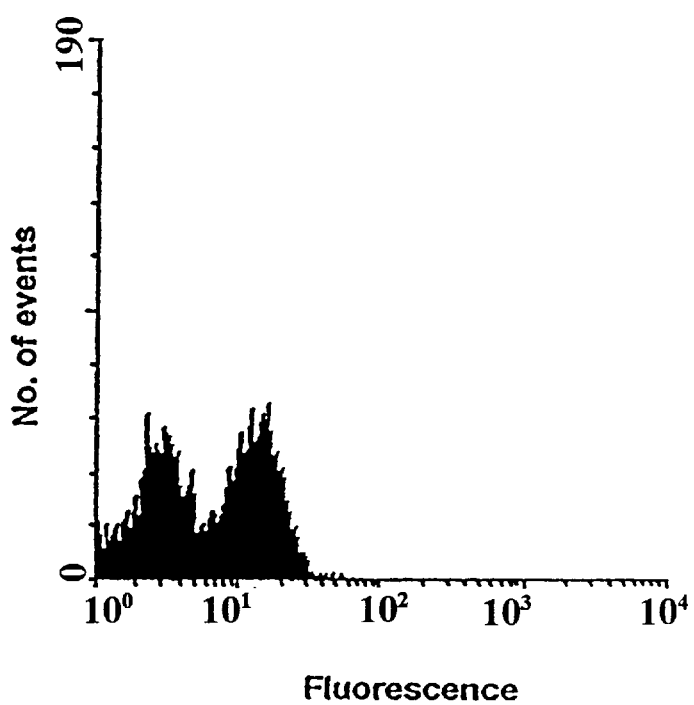

Prior studies of IL-8/NAP-1 have demonstrated that this cytokine induces an increase in Ca after stimulation of neutrophils. FIG. 8B demonstrates the effect of 77 amino acid IL-8 at $10^{-6}$M on neutrophil Ca release as measured and described in example III as compared to PMN prior to stimulation (FIG. 8A). This should be as compared to FIGS. 9A, B showing the lack of effects by the excipient alone. Similarly, the low molecular weight peptide, Analog 1, from residues 4–20 induced a change in neutrophil Ca concentrations as shown in FIGS. 10A and B. Upon addition of IL-8/NAP-1 or residues 4–20, the majority of neutrophils showed an increase in calcium concentration which is identical one to another.

EXAMPLE VI

Chemokines form a superfamily that is divided into two distinct functional classes: alpha and beta. All the members of each class share an organizing primary sequence motif. Alpha family members are distinguished by the C-X-C motif—where the first two cysteines of the motif are separated by an intervening residue. C-X-C chemokines are potent chemoattractants and activators for neutrophils. The beta family chemokines have a C—C motif and are equally potent chemoattractants and activators of monocytes. However, other roles are rapidly emerging for chemokines as well. Thus, both alpha and beta chemokines, have been shown to attract both memory T-cells and eosinophils as well as trigger the release of histamine from basophils.

Edgington, discussed in Bio/Technology (1993, 11:676) the potential to design site specific inhibitors and/or agonists for the chemokines. He states that most researchers believe that the greatest promise lies in creating small molecular peptides or mimetics that will compete with natural molecules for the chemokine binding sites. Because both the ligand and the receptor binding site are relatively small, drug designers have focused on understanding where the critical contact points lie that turn on the receptor signal transduction machinery. Many of these investigators believe that similarities in sequence will also yield structural similarities. Dr. Daniel Witt of Repligen, Cambridge, Mass. is quoted in the article as saying "If you have 15 different receptors and you know the crystal structure for two you can expect the structural model will hold true for all." It was suggested that both chimeric ligands and receptors should fold properly and yield data about critical contact points. "As a system, it is about everything you could ask for imposing structural-functional questions" i.e., there is strong homology amongst the receptors and ligands of the chemokines which will facilitate rational drug design. It is clear that existing drugs have been synthesized which target similar membrane spanning receptors including: histamine inhibitors, beta blockers, and serotonin receptors which have all yielded receptor antagonists to date.

"Receptor promiscuity" presents one problem to drug design of the chemokines. Within chemokine families, individual receptors bind multiple ligands. Determining chemokine structure and function after dispensing with the dogma of one ligand, one receptor is extremely difficult especially when target cells contain an ensemble of receptors on their membrane. For example, there are at least three kinds of chemokine receptors involved in binding the beta chemokines MCP-1, MIP-1α/β and RANTES. Based on studies to date one receptor binds all three ligands, another binds only MIP-1α/β and a third only binds MCP-1. Similar observations of receptor/ligand promiscuity are seen with the alpha chemokines. High affinity binding to neutrophils is observed for IL-8; however, evidence for high and low affinity binding receptors is observed with NAP-2, ENA-78 and MGSA. Two closely related neutrophil derived IL-8 receptors, type A and type B, have been cloned whose binding characteristics could account for the binding observed with neutrophils: Type A receptors have a high affinity for IL-8 and low affinity for MGSA and NAP-2. The type B receptors bind IL-8 and MGSA with high and NAP-2 with intermediate affinity. However, it remains possible that more than two IL-8 receptors exist and are expressed on neutrophils.

EXAMPLE VII

Platelet factor 4 (PF-4) is carried within the alpha granules of platelets in the form of a non-covalent complex. PF-4 is a tetramer of four identical polypeptide chains, each of which contains 70 residues in the human moieties. When released into the plasma from activated platelets, PF-4 attracts white blood cells i.e., neutrophils and monocytes and it's release may be a signal that is involved in inflammation. Other possible functions of PF-4 derive from a strong binding to negatively charged polysaccharides especially heparan and heparin for which it has a dissociation constant of $10^{-7.5}$. The ability of PF-4 to neutralize heparin and related polymers is of general interest because heparin has been shown to interact with over 50 different enzymes to suppress muscle growth and to accelerate angiogenesis in solid tumors. PF-4 has recently been patented as Oncostatin A for its ability to inhibit tumor growth. It has also been shown to reverse immunosuppression in mice.

PF-4 also binds tightly and preferentially to double stranded DNA in vitro. This binding probably does not occur in vivo but it might be an important attribute of several recently discovered growth related proteins which are homologous to PF-4. Members of this class are 1) induced by IFN-γ, 2) constitutively overexpressed in Chinese hamster and human cell lines, 3) strongly induced by Rous sarcoma virus and fibroblast cells and 4) over expressed in stimulated leukocytes.

In contrast to many of the other alpha chemokines, PF-4 does not induce comparable neutrophil responses although chemotaxis and exocytosis have been reported with concentrations that were 1000:10000-fold higher than those required for IL-8.

PF-4 crystallizes as a tetramer, although the monomer structure is similar to that of IL-8. In solution, human PF-4 is in equilibrium among monomers, dimers, and tetramers. PF-4 and IL-8 share 35% sequence identity, including the four cysteines. Molecular modeling studies suggest that a similar folding pattern will be found for all members of the C-X-C family. Even MCP which belongs to the C—C family (beta chemokine), has been found to have the same tertiary structure. Thus, it will be possible based on example VI and VII to sequence an agonist for PF4.

EXAMPLE VIII

Platelet basic protein (PBP) is a highly specific platelet alpha granular protein that is a precursor of low affinity platelet factor 4 (LA-PF4) and beta thromboglobulin (βTG). These proteins differ only in amino terminal amino acid sequence and isoelectric point. PBP is synthesized by megakaryocytes, contains 94 amino acids and is converted to LA-PF4 which contains 85 amino acid residues within megakaryocyte and platelet granules. βTG itself (81 amino acid residues) as originally described cannot be detected in cell lysates prepared using trichloroacetic acid. It probably results from amino terminal cleavage of LA-PF4 or PBP after cell secretion. Production of βTG from PBP and LA-PF4 can be demonstrated in vitro by incubating the platelet release supernatant at 37° C. or by limited cleavage with plasmin or trypsin. The three forms of βTG antigen are immunologically identical when using rabbit polyclonal antibodies. The biological activities of PBP and its derivatives are not well understood. It has been proposed that LA-PF4 [also referred to as connective tissue activating peptide III (CTAP-III)] is a weak mitogen for connective tissue fibroblasts. It has also been reported that βTG also is an antigen that also promotes chemotaxis in fibroblasts. In recent studies, it was observed that a cleavage product of βTG called neutrophil activating peptide (NAP-2) was formed in cultured and stimulated mononuclear cells and is a potent activator of human neutrophils. NAP-2 is a 78 amino acid peptide corresponding to the major carboxy-terminal fragment of βTG. It has 46% homology with NAP-1/IL-8. NAP-2 behaves as a typical chemotactic receptor agonist, including cytosolic free Ca changes, chemotaxis, and exocytosis while PBB, LA-PF4 and PF4 have little such activity. It should be noted, as discussed above, that it also interacts with the NAP-1/IL-8 receptors. Thus, based on example VI and VIII it should be possible to synthesize agonists for NAP-2, including binding to the IL-8 beta receptor.

EXAMPLE IX

IP-10 was originally isolated as a predominate messenger RNA form induced by IFN-γ or LPS in monocytes and its expression has been detected in vivo during the development of a delayed type hypersensitivity cellular immune response by monocytes, endothelial cells, and infiltrating mononuclear cells. In addition, IP-10 expression has been seen in the epidermis, dermis and cutaneous lesions of psoriasis, tuberculoid leprosy, and fixed drug eruptions.

IP-10 is a member of the chemokine superfamily and is approximately 30% homologous to IL-8 and PF-4. Recent studies have shown that IP-10 can elicit an anti-tumor inflammatory response that is capable of inhibiting the growth of plasmacytoma and mammary adenocarcinoma in immunocompetent mice. This effect is thymus dependent suggesting that IP-10 might act on T-cells. In addition, a neutrophil, and monocytic accumulation is seen as a result of IP-10 expression in immunocompetent but not nude mice. IP-10 does not have an ELR motif. ELR incorporation into IP-10 is not sufficient for IL-8 receptor interaction or neutrophil activation and suggests that IP-10 has a different receptor ligand confirmation. However, hybrids formed between IL-8 and IP-10 could be designed which demonstrate that essential receptor binding motifs from the IL-8 sequence could be structured within the IP-10 molecule allowing IL-8 binding.

Recent reports have shown that IP-10 is expressed by activated but not by resting T-hybridoma cells, normal T-cells and thymocytes. While resting lymphocytes did not synthesize IP-10, a high level of IP-10 transcripts are found in lymphoid organs (spleen, thymus, and lymph nodes). Thymic and splenic stromal cells constitutively express high levels of both IP-10 messenger RNA and protein accounting for the high level of spontaneous expression in lymphoid tissue. Therefore, in addition to its role as a proinflammatory cytokine, IP-10 may participate in T-cell effector function of perhaps T-cell development. IP-10 expression has also been shown to be induced in delayed type contact hypersensitivity in sensitized animals. Thus, based on example VI and IX we will be able to synthesize agonists for IP-10.

EXAMPLE X

Human tumors can constitutively express cytokines and growth factors. Melanoma cells constitutively express GRO-α which is also termed melanoma growth stimulatory activity. Similarly, GRO-α is expressed in human colon tumors along with GRO-β and GRO-γ. These three genes, GRO-α, GRO-β, and GRO-γ, are closely linked on chromosome 4. GRO-β and GRO-γ show 90 and 86% sequence homology with GRO-α. The GRO-α/MGSA alpha chemokine has potent chemotactic, growth regulatory and transformative functions. The function of GRO-β and GRO-γ is unknown. GRO-α messenger RNA is selectively overexpressed in psoriasic epidermis and is reduced by therapy with Cyclosporin-A. It has been suggested that this over expression is a keratinocyte response to activated T-cells in psoriasis. GRO-α/MGSA has been localized in a variety of cutaneous lesions. A raised level of immunoreactive GRO-α/MGSA in diseased epidermis is detected in verruca vulgaris followed by psoriasis, keratoacanthoma, and squamous cell carcinoma. Detection of GRO-α in basal cell carcinoma is variably present in the sclerosis variant and absent in the more common nodular variant. Thus, based on example VI and X we will be able to synthesize agonists for GRO-α, β, and Γ.

EXAMPLE XI

Recently, another alpha chemokine has been discovered and has been called ENA-78 (epithelial cell derived neutrophil activator). ENA-78 shows significant amino acid sequence homology with NAP-2 (53%), GRO-α (52%), and IL-8 (22%). ENA-78 appears to activate neutrophils through the IL-8 receptor. ENA-78 has been cloned in pigs and was initially described as alveolar macrophage derived chemotactic factor 2. It shares 53% sequence homology with human NAP-2 and 61% sequence homology with the GRO-related proteins. It also has 67% sequence homology with the 78 amino acid ENA-78 and is felt to represent the porcine variant thereof. ENA-78 was initially identified in the conditioned medium of stimulated human epithelial cell line A549. It is produced in response to stimulation with either IL-1β or TNF-α and is produced and secreted concomitantly with IL-8, GRO-α, and GRO-γ. ENA-78 consists of 78 amino acids and has a molecular weight of 8357. The four cysteines are positioned identically to those of IL-8 and similar analogues. ENA-78 stimulates neutrophils, induces chemotaxis, a rise in intracellular-free Ca and exocytosis. Cross desensitization experiments indicate that ENA-78 acts through the same type of receptors as IL-8, NAP-2 and GRO-α. Thus, based on examples VI and XI, we will be able to synthesize agonists for ENA-78 including peptide analogs that bind to the IL-8 receptor.

While the invention has been disclosed in this patent application by reference to the details of preferred embodiments of the invention, it is to be understood that this disclosure is intended in an illustrative rather than in a limiting sense, as it is contemplated that modifications will readily occur to those skilled in the art, within the spirit of the invention and the scope of the appended claims.

---

What is claimed is:

1. A peptide of up to 27 amino acids in length, having agonistic activity for alpha chemokines, said peptide comprising an amino acid sequence having the formula:

Glu-Leu-Arg-Cys-$Xaa_1$-Cys-$Xaa_2$-$Xaa_3$-$Xaa_4$-$Xaa_5$-$Xaa_6$-$Xaa_7$-$Xaa_8$-$Xaa_9$-$Xaa_{10}$-$Xaa_{11}$-$Xaa_{12}$ (SEQ ID NO:12)

wherein
$Xaa_1$ is Gln, Met, Leu, Thr, or Val;
$Xaa_2$ is Ile, Leu, or Val;
$Xaa_3$ is Lys, Gln, or Ser;
$Xaa_4$ is Thr, or Ile;
$Xaa_5$ is Tyr, Leu, Met, His, Val, Asn, or Thr;
$Xaa_6$ is Ser, Gln, Thr, Leu, Met, Val or Ala;
$Xaa_7$ is Lys, Arg, Gly, or His;
$Xaa_8$ is absent or is Pro, Phe, Ile, Val, His, or Gly;
$Xaa_9$ is absent or is Phe, Ile, Gly, or Val;
$Xaa_{10}$ is absent or is His, Lys, or Arg;
$Xaa_{11}$ is absent or is Pro, Leu, or Phe;
$Xaa_{12}$ is absent or is Lys, His or Arg; and wherein the amino acid residue Glu in said formula forms the amino terminus of the peptide and at least one Cys residue in said peptide is optionally substituted by an amino acid selected from the group consisting of diaminosuberic acid, homocysteine, or aminobutyric acid.

* * * * *